US012203096B2

(12) United States Patent
Li et al.

(10) Patent No.: US 12,203,096 B2
(45) Date of Patent: Jan. 21, 2025

(54) PREPARATION, EXPANSION, AND USES OF ADULT PLURIPOTENT STEM CELLS

(71) Applicant: The Board of Trustees of the Leland Stanford Junior University, Stanford, CA (US)

(72) Inventors: Shaowei Li, Newark, CA (US); Min Hu, Newark, CA (US); Hermann Peter Lorenz, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/953,216

(22) Filed: Sep. 26, 2022

(65) Prior Publication Data
US 2023/0021683 A1 Jan. 26, 2023

Related U.S. Application Data

(62) Division of application No. 16/500,793, filed as application No. PCT/US2018/025846 on Apr. 3, 2018.

(Continued)

(51) Int. Cl.
*C12N 5/074* (2010.01)
*A61K 35/28* (2015.01)

(52) U.S. Cl.
CPC ............ *C12N 5/0607* (2013.01); *A61K 35/28* (2013.01); *C12N 2502/14* (2013.01)

(58) Field of Classification Search
CPC .. C12N 5/0607; C12N 2502/14; A61K 35/28; A61K 35/30; A61K 35/12
See application file for complete search history.

(56) References Cited

U.S. PATENT DOCUMENTS 9,657,267 B2    5/2017  Izadyar et al.
2006/0205075 A1 9/2006  Nakatsuji et al.
(Continued)

FOREIGN PATENT DOCUMENTS

CN    102884177 A    1/2013
JP    2011519574 A    7/2011
(Continued)

OTHER PUBLICATIONS

Nakamura et al ("Angiopoietin-1 supports induction of hematopoietic activity in human CD34-bone marrow cells," Experimental Hematology 35 (2007) 1872-1883 (Year: 2007).*

(Continued)

*Primary Examiner* — Marcia S Noble
*Assistant Examiner* — Briana N Ebbinghaus
(74) *Attorney, Agent, or Firm* — Sheppard Mullin Richter & Hampton LLP

(57) ABSTRACT

Certain relatively small cells present in the periphery blood of mammals can be activated to form pluripotent stem cell populations. These small cells are generally less than five micrometers in diameter and are CD45-positive, and are referred to herein as CD45$^+$ cells or dormant tiny cells. Accordingly, provided are cell populations and compositions with enriched dormant tiny cells from blood samples and methods and compositions for activating these dormant tiny cells. Upon differentiation, the activated stem cells can be used for various therapeutic purposes.

6 Claims, 24 Drawing Sheets

Related U.S. Application Data

(60) Provisional application No. 62/481,554, filed on Apr. 4, 2017.

(56) References Cited

U.S. PATENT DOCUMENTS

| | | | |
|---|---|---|---|
| 2009/0155226 A1* | 6/2009 | Kong | C12N 5/0607 435/372 |
| 2010/0227396 A1 | 9/2010 | Lim et al. | |
| 2011/0033428 A1 | 2/2011 | Maruyama et al. | |
| 2013/0280219 A1 | 10/2013 | Shiels | |
| 2016/0097036 A1 | 4/2016 | Chaurasia et al. | |
| 2017/0136152 A1 | 5/2017 | Izadyar et al. | |

FOREIGN PATENT DOCUMENTS

| | | |
|---|---|---|
| JP | 2013514760 A | 5/2013 |
| JP | 2014073084 | 4/2014 |
| WO | WO2003026584 A2 | 4/2003 |
| WO | 2007118680 A2 | 10/2007 |
| WO | WO2017115268 A1 | 7/2017 |
| WO | 2017176267 A1 | 10/2017 |
| WO | 2017218846 A1 | 12/2017 |
| WO | 2018187298 A1 | 10/2018 |
| WO | 2020061557 A1 | 3/2020 |

OTHER PUBLICATIONS

De Paiva et al ("Cell Size Correlates with Phenotype and Proliferative Capacity in Human Corneal Epithelial Cells," Stem Cells 2006;24:368-375) (Year: 2006).*

Kaiser et al ("BM cells giving rise to MSC in culture have a heterogeneous CD34 and CD45 phenotype," Cytotherapy (2007) vol. 9, No. 5, 439-450 (Year: 2007).*

Soncin et al ("The Function of E-Cadherin in Stem Cell Pluripotency and Self-Renewal," Genes 2011, 2, 229-259 (Year: 2011).*

Wu et al ("Epigenetic Regulation of Stem Cell Differentiation," Pediatric Research vol. 59, No. 4, Pt 2, 2006) (Year: 2006).*

Watanabe-Susaki et al ("Biosynthesis of Ribosomal RNA in Nucleoli Regulates Pluripotency and Differentiation Ability of Pluripotent Stem Cells," Stem Cells 2014;32:3099-3111) (Year: 2014).*

Li et al ("Human Hepatic Progenitor Cells Express Hematopoietic Cell Markers CD45 and CD109," Int J Med Sci. 2014; 11(1): 65-79) (Year: 2014).*

Bordoni et al ("Hepatocyte-Conditioned Medium Sustains Endothelial Differentiation of Human Hematopoietic-Endothelial Progenitors." Hepatology, vol. 45, No. 5, 2007). (Year: 2007).*

Mallanna et al ("Differentiation of hepatocytes from pluripotent stem cells;" Curr Protoc Stem Cell Biol Sep. 20, 2014). (Year: 2014).*

Stecklum et al ("Cell differentiation mediated by co-culture of human umbilical cord blood stem cells with murine hepatic cells," In Vitro Cell.Dev.Biol.—Animal (2015) 51:183-191 (Year: 2015).*

Rogers et al. Identification and analysis of in vitro cultured CD45-positive cells capable of multi-lineage differentiation. Exp Cell Res. May 15, 2007;313(9):1839-52. (Year: 2007).*

Ghaneialvar et al. Characterization and Classification of Mesenchymal Stem Cells in Several Species Using Surface Markers for Cell Therapy Purposes Indian J Clin Biochem. Jan. 2018; 33(1): 46-52. (Year: 2017).*

Campioni et al. Loss of Thy-1 (CD90) antigen expression on mesenchymal stromal cells from hematologic malignancies is induced by in vitro angiogenic stimuli and is associated with peculiar functional and phenotypic characteristics. Cytotherapy. 2008; 10(1):69-82. (Year: 2008).*

Liu et al. Loss of E-cadherin and epithelial to mesenchymal transition is not required for cell motility in tissues or for metastasis. Tissue Barriers. 2014; 2(4): e969112. (Year: 2014).*

Lin et al. Is CD34 Truly a Negative Marker for Mesenchymal Stem Cells ?. Cytotherapy. Nov. 2012;14(10):1159-63. (Year: 2012).*

Chen et al. Resolving the distinct stages in erythroid differentiation based on dynamic changes in membrane protein expression during erythropoiesis. Proc Natl Acad Sci U S A. Oct. 13, 2009; 106(41):17413-8.; (Year: 2009).*

Ding et al., "ABCG2: A potential marker of stem cells and novel target in stem cell and cancer therapy," Life Sciences, 2010, vol. 86, Issues 17-18, pp. 631-637.

Dupas et al., "Fetal muscle contains different CD34+ cell subsets that distinctly differentiate into adipogenic, angiogenic and myogenic lineages," Stem Cell Research, 2011, vol. 7, Issue 3, pp. 230-243.

Invitrogen by Thermo Fisher Scientific U.S. Appl. No. 16/579,235.

Li et al., "Peripheral Blood-Derived Mesenchymal Stem Cells: Candidate Cells Responsible for Healing Critical-Sized Calvarial Bone Defects," Stem Cells Translational Medicine, 2015, pp. 359-368.

Bahlmann et al., "Erythropoietin Regulates Endothelial Progenitor Cells", Blood, The American Society of Hematology, vol. 103, No. 3, Feb. 1, 2004, pp. 921-926.

Kong et al ("Germ plasm-like Dot cells maintain their wound regenerative function after in vitro expansion," Clinical and Experimental Pharmacology and Physiology (2010) 37, e136-e144)( (Year: 2010).

Hu et al., "Expansion and Hepatic Differentiation of Adult Blood-Derived CD34 + Progenitor Cells and Promotion of Liver Regeneration After Acute Injury", Stem Cells Translational Medicine, vol. 5, No. 6, Apr. 13, 2016, pp. 723-732.

Kucia et al., A Population of Very Small Embryonic-like (VSEL) CXCR4+SSEA-1+Oct4+ Stem Cells Identified in Adult Bone Marrow, Blood Cancer Journal, vol. 20, Jan. 1, 2006, pp. 857-869.

Li et al., "Treatment of Full-Thickness Skin Wounds with Blood-Derived CD34 + Precursor Cells Enhances Healing with Hair Follicle Regeneration", Advances in Wound Care, vol. 9, No. 5, May 1, 2020, pp. 264-276.

Nakamura et al., "Angiopoietin-1 Supports Induction of Hematopoietic Activity in Human CD34-Bone Marrow Cells", Experimental Hematology 35, Dec. 2007, vol. 35, No. 12, pp. 1872-1883.

Park et al., "Human Embryonic Stem Cell-Derived Hematoendothelial Progenitors Engraft Chicken Embryos", Experimenal Hematology, vol. 37, No. 1, Jan. 1, 2009, pp. 31-41.

Watanabe-Susaki et al ("Biosynthesis of Ribosomal RNA in Nucleoli Regulates Pluripotency and Differentiation Ability of Pluripotent Stem Cells," Stem Cells 2014;32:3099-3111) (Watanabe-Susaki). (Year: 2014).

Li 35, Qiuhui December et al: 1, "Cancer 2015, stem Pages cells 191-199, and cell doi.size: A causal link?" org/10.1016/j.semcancer. 2015.07.002, Seminars in Cancer (25 Biology, pages) vol. 35. Dec. 1, 2015, pp. 191-199, doi.org/10.1016/j.semcancer.2015.07.002, (25 pages).

Krebsbach, Paul H., et al: "The Role of Integrin α6 (CD49f) in Stem Cells: More than a Conserved Biomarker" Stem Cells and Development, vol. 26, No. 15, Aug. 1, 2017, pp. 1090-1099, xp055920751, doi: 10.1089/scd.2016.0319, (10 pages).

Ono et al., "CD34 and CD49f Double-Positive and Lineage Marker-Negative Cells Isolated from Human Myometrium Exhibit Stem Cell-Like Properties Involved in Pregnancy-Induced Uterine Remodeling", Biology of Reproduction, Jun. 24, 2015, vol. 93, No. 2, pp. 1-9.

Zeng et al., "Lack of ABCG2 expression and side population properties in human pluripotent stem cells", Stem Cells, Auqust 7, 2009, vol. 27, Issue 10, pp. 2435-2445.

* cited by examiner

PREPARATION, EXPANSION, AND USES OF ADULT PLURIPOTENT STEM CELLS

CROSS REFERENCE TO RELATED APPLICATIONS

This application is a division of U.S. application Ser. No. 16/500,793, filed Oct. 3, 2019, which is a United States National Stage of International Application No. PCT/US2018/025846, filed Apr. 3, 2018, which claims the benefit under 35 U.S.C. § 119(e) of U.S. Provisional Application Ser. No. 62/481,554, filed Apr. 4, 2017, the content of each of which is incorporated by reference in its entirety into the present disclosure.

BACKGROUND

The identification and characterization of stem cells is a major focus of regenerative medicine. Stem cells are able to self-renew, a property that ensures their ability to survive and produce post-mitotic cells necessary for maintenance of tissue homeostasis. Along with the ability of self-renewal, a stem cell has the ability to differentiate into some or all of the cell types required to maintain homeostasis within a particular tissue, organ system, or even an entire organism.

The developmental stage at which a stem cell is isolated usually determines what types of cells it can differentiate into. For example, embryonic stem (ES) cells, which are isolated from the inner cell mass of the blastocyst, are pluripotent and can differentiate into any of the three germ layers (endoderm, mesoderm, and ectoderm). Adult or somatic stem cells found in various adult tissues (e.g., bone marrow, adipose tissue, blood, etc.), however, are typically more limited with respect to differentiation and thus are considered multipotent, oligopotent or unipotent. Adult stem cells include several types such as hematopoietic stem cells (HSCs), mesenchymal stem cells (MSCs), endothelial stem cells (ESCs), mammary stem cells (MaSCs), intestinal stem cells (ISCs), neural stem cells (NSCs), adult olfactory stem cells (OSCs), neural crest stem cells (NCSCs), and testicular stem cells (TSCs). Induced pluripotent stem cells (also known as iPS cells or iPSCs) are a type of pluripotent stem cells that can be generated directly from somatic cells by introducing specific sets of pluripotency-associated genes, or "reprogramming factors". Other types of stem cells have also been reported, the existence of which is still controversial.

For over 30 years, bone marrow has been used to treat cancer patients with conditions such as leukemia and lymphoma. This is the only form of stem-cell therapy that is widely practiced. With respect to embryonic stem cells, human embryonic stem cell (hESC) research is ethically and politically controversial because it involves the destruction, or at least manipulation, of human embryos. Tumorigenicity of hESCs is also a clinical hurdle for cell therapies using hESCs. Further, it has so far not been feasible to create patient-matched embryonic stem cell lines. With respect to the iPSCs, the reprogramming of somatic cells to produce iPSCs avoids the ethical problems specific to hESC research. However, the production of iPSCs requires genetic alteration/modification, which have also been linked to cancer in one way or another. Non-genetic methods of producing iPSCs, for example using recombinant proteins, generally have low efficiency. Thus the iPSC technology has not yet advanced to a stage where therapeutic transplants have been deemed safe. With respect to adult stem cells, their use in research and therapy is not considered to be controversial. However, unlike the pluripotent stem cells, the adult stem cells are restricted to certain types or "lineages". Consequently, adult stem cell therapies require a stem cell source of the specific lineage needed, and harvesting and/or culturing them up to the numbers required is a challenge.

Therefore, identification of pluripotent stem cells from adult tissue without the need of genetic manipulation, and establishing a protocol for culturing them in vitro will pave the way for practical cell-based therapy of tissue repair and regeneration. Such pluripotent stem cells isolated from adult tissue will also provide new therapeutics for unmet medical needs in chronic and aging related diseases.

A cell culture system would be a powerful asset for the investigation and development of stem cells. One of the biggest challenges in the field is to establish a model that will enable quick expansion and efficient and precise differentiation of stem cells in vitro. Such a model must have the capability of providing a large quantity of homogeneous cells that can undergo targeted and controllable differentiation under certain culture conditions. Currently, there is no generally accepted sustainable cell culture model for pluripotent stem cells that meet therapeutic requirements. In addition, current pluripotent stem cells have various issues and flaws in processes such as isolation, in vitro expansion, and/or induction of differentiation, which would impede the use of current pluripotent stem cells in clinical applications and therapeutic uses.

Therefore, there is a need for identification of pluripotent stem cells from adult tissue without genetic manipulation, which can quickly expand in vitro, have high efficiency in differentiation, and are non-tumorigenic. There is also a need for the establishment of a protocol for culturing the pluripotent stem cells in vitro for cell-based therapy.

SUMMARY

The identification of expandable, pluripotent stem cells from the adult tissue and the establishment of a protocol for culturing them in vitro will pave the way for practical cell-based therapy of tissue repair and regeneration.

The present disclosure provides a composition comprising at least 1000 cells, and at least 50% of the cells are CD45$^+$ cell that express CD45 and have a diameter of less than 5 μm. In some aspects, the CD45$^+$ cells are further characterized as positive in CD34 and negative in ABCG2. In some aspects, less than 20% of the cells are red blood cells. In some aspects, the CD45$^+$ cells are further characterized as negative in Lin. In some aspects, the CD45$^+$ cells further express one or more markers selected from the group consisting of CD44, CD150, Sca1, c-kit, Thy1.1(CD90.1), Oct 4, SSEA1, Nanog, Vasa, CD133, and CD105. In some aspects, the CD45$^+$ cells do not express one or more markers selected from the group consisting of CD41, Lin, E-cadherin, and CD184 (CXCR4). In some aspects, the CD45$^+$ cells can be activated by a medium comprising one or more factors, and the activated cells express ABCG2.

Also provided is a method of preparing the composition as disclosed herein, comprising (1) removing at least a portion of red blood cells from a blood sample; (2) removing at least a portion of platelets from the sample; (3) centrifuging the sample at 400×g-3000×g; and (4) obtaining a pellet that comprises the composition as disclosed herein. In some aspects, in step (3) the sample is centrifuged at a speed of at least 3000×g.

Also provided is method of culturing cells, comprising culturing a plurality of mammalian cells in a medium that is in contact with or has been conditioned with at least one selected from the group consisting of primary hepatocytes, human hepatoblastoma (HepG2) cells, a hepatocyte cell line, and a mouse embryo fibroblast (MEF) cell line. In some aspects, the hepatocyte cell line comprises AML12, HepaRG, or the combination thereof. In some aspects, the mammalian cells (a) have a diameter of less than 5 μm, and (b) express CD45. In some aspects, wherein the cells are further characterized as positive in CD34 and negative in ABCG2. In some aspects, the mammalian cells include one or more types of stem cells.

The present disclosure further provides an isolated mammalian cell that expresses CD34 and ABCG2, and does not express CD45. In some aspects, the mammalian cell is further characterized as positive in Oct4, Nanog, and/or keratin epithelium, and negative in Lin. In some aspects, the mammalian cell further expresses one or more markers selected from the group consisting of CD117, CD29, CD44, CD73, CD90, CD105, Sca1, CD31, CD184, Nestin, and Osteocalcin. In some aspects, the mammalian cell does not express one or more markers selected from the group consisting of CD3, CD4, CD8a, CD11b, CD13, CD140a, E-cadherin, and Lin. Also provided is a population of the cells as disclosed herein.

Also provided is a stem cell derived from a cell that (a) has a diameter of less than 5 μm, (b) expresses CD45, and (c) does not express ABCG2, wherein the stem cell expresses ABCG2, and is further characterized as (a) $CD34^+/CD45^+$; (b) $CD34^+/CD45^-$; (c) $CD34^-/CD45^+$; or (d) $CD34^-/CD45^-$. The embodiments of the disclosure also provide a cell differentiated from the stem cell as disclosed herein.

Also provided is a composition comprising the stem cells, as disclosed herein, in a pharmaceutically acceptable carrier or excipient. In some embodiments, also provided is a composition comprising the differentiated cells, as disclosed herein, in a pharmaceutically acceptable carrier or excipient. Also provided is a method of treating a disease or condition in a subject in need thereof, comprising administering an effective amount of the composition as disclosed herein to the subject.

DETAILED DESCRIPTION

Figure 1:
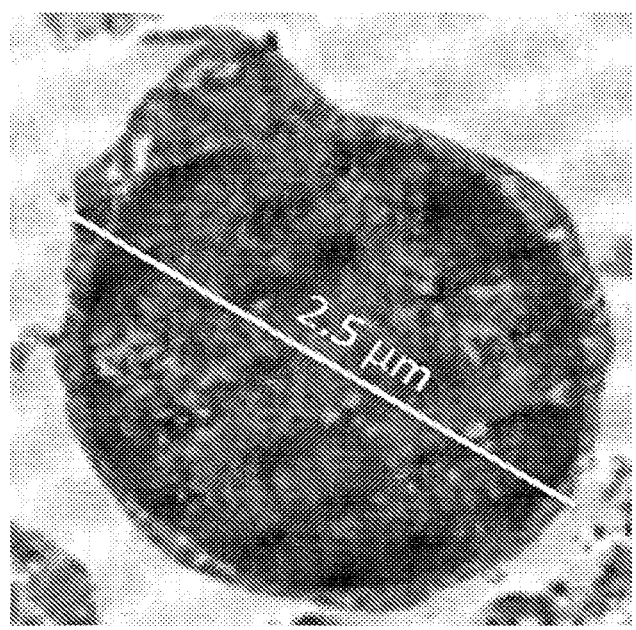
FIG. 1 shows an electron microscope image of a dormant tiny cell isolated from blood.

Throughout this disclosure, various publications, patents and published patent specifications are referenced herein. The disclosures of these publications, patents and published patent specifications are hereby incorporated by reference in their entirety into the present disclosure.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (Cold Spring Harbor Laboratory Press (2002)); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Harlow and Lane, eds. (1999) Using Antibodies, A Laboratory Manual; Animal Cell Culture (R. I. Freshney, ed. (1987)); Zigova, Sanberg and Sanchez-Ramos, eds. (2002) Neural Stem Cells.

All numerical designations, e.g., pH, temperature, time, concentration, and molecular weight, including ranges, are approximations which are varied (+) or (−) by increments of 0.1 or 1 where appropriate. It is to be understood, although not always explicitly stated that all numerical designations are preceded by the term "about". The term "about" also includes the exact value "X" in addition to minor increments of "X" such as "X+0.1 or 1" or "X−0.1 or 1", where appropriate. It is also to be understood, although not always explicitly stated, that the reagents described herein are merely exemplary and that equivalents of such are known in the art.

1. Definitions

Unless defined otherwise, all technical and scientific terms used herein have the same meaning as commonly understood by one of ordinary skill in the art to which this disclosure belongs. As used herein the following terms have the following meanings.

As used in the specification and claims, the singular forms "a", "an", and "the" include plural referents unless the context clearly dictates otherwise. Thus, for example, reference to "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

As used herein, the term "isolated" means separated from constituents, cellular and otherwise, in which the cell, tissue, polynucleotide, peptide, polypeptide, protein, antibody or fragment(s) thereof, which are normally associated in nature. For example, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. An isolated cell is a cell that is separated from tissue or cells of dissimilar phenotype or genotype.

As used herein, "stem cell" defines a cell with the ability to divide for indefinite periods in culture and give rise to specialized cells. Non-limiting examples of types of stem cells include somatic (adult) stem cells, embryonic stem cells, parthenogenetic stem cells (see Cibelli et al. (2002) Science 295(5556):819; U.S. Patent Publ. Nos. 20100069251 and 20080299091), and/or induced pluripotent stem cells (iPS cells or iPSCs). A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. Non-limiting examples of embryonic stem cells include the HES2 (also known as ES02) cell line available from ESI, Singapore and the H1 or H9 (also known as WA01) cell line available from WiCell, Madison, WI Additional lines are pending NIH review. See, for example, grants.nih.gov/stem_cells/registry/current.htm (last accessed Mar. 13, 2017). Pluripotent embryonic stem cells can be distinguished from other types of cells by the use of markers including, but not limited to, Oct-4, alkaline phosphatase, CD30, TDGF-1, GCTM-2, Genesis, Germ cell nuclear factor, SSEA1, SSEA3, and SSEA4. An induced pluripotent stem cell (iPSC) is an artificially derived stem cell from a non-pluripotent cell, typically an adult somatic cell, produced by inducing expression of one or more stem cell specific genes. An iPSC expresses specific genes including, but are not limited to, the family of octamer transcription factors, e.g., Oct-3/4; the family of Sox genes, e.g., Sox1, Sox2, Sox3, Sox 15 and Sox 18; the family of Klf genes, e.g., Klf1, Klf2, Klf4 and Klf5; the family of Myc genes, e.g., c-myc and L-myc; the family of Nanog genes, e.g., Octamer-4 (OCT4), NANOG and REX1; or LIN28. Examples of iPSCs are described in Takahashi et al. (2007) Cell advance online publication 20 Nov. 2007; Takahashi & Yamanaka (2006) Cell 126:663-76; Okita et al. (2007) Nature 448:260-262; Yu et al. (2007) Science advance online publication 20 Nov. 2007; and Nakagawa et al. (2007) Nat. Biotechnol. Advance online publication 30 Nov. 2007.

As used herein, the term "propagate" means to grow or alter the phenotype of a cell or population of cells. The term "grow" or "expand" refers to the proliferation of cells in the presence of supporting media, nutrients, growth factors, support cells, or any chemical or biological compound necessary for obtaining the desired number of cells or cell type. In one embodiment, the growing/expansion of cells results in the regeneration of tissue.

As used herein, the term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

As used herein and as set forth in more detail below, "conditioned medium" is medium which was cultured with a mature cell that provides cellular factors to the medium such as cytokines, growth factors, hormones, extracellular matrix, and some materials that would facilitate cell growth, development, and differentiation.

As used herein, the term "differentiation" describes the process whereby an unspecialized cell acquires the features of a specialized cell such as a skin, heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell.

As used herein, the "lineage" of a cell defines the heredity of the cell, i.e. its predecessors and progeny. The lineage of a cell places the cell within a hereditary scheme of development and differentiation. As used herein, "a cell that differentiates into a mesodermal (or ectodermal or endodermal) lineage" defines a cell that becomes committed to a specific mesodermal (or ectodermal or endodermal) lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to cells that give rise to the pancreas, liver, lung, stomach, intestine, and thyroid.

As used herein, the term "pluripotent stem cells" refers to cells that are: (i) capable of indefinite proliferation in vitro in an undifferentiated state; (ii) maintain a normal karyotype through prolonged culture; and (iii) maintain the potential to differentiate to derivatives of all three embryonic germ layers (endoderm, mesoderm, and ectoderm) even after prolonged culture. Non-limiting examples of currently available pluripotent stem cells include embryonic stem cells and iPSCs. As used herein, the term "embryonic-like" stem cells refers to cells derived from tissues, organs, or blood, possessing pluripotent characteristics of embryonic stem cells.

As used herein, the term "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm, or endoderm), or from different germ layers. An example of two progeny cells with distinct developmental lineages from differentiation of a multi-lineage stem cell is a myogenic cell and an adipogenic cell (both are of mesodermal origin, yet give rise to different tissues). Another example is a neurogenic cell (of ectodermal origin) and adipogenic cell (of mesodermal origin).

As used herein, the term "self-renewable" refers to a cell being able to self-renew for over a number of passages without substantial changes of cell properties. In one aspect, the number of passages is at least about 5, or alternatively at least 10, or alternatively at least about 15, 20, 30, 50, or 100.

As used herein, the term "substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively more than 95%, or alternatively more than 99% of the cells are of the same or similar phenotype. Phenotype can be determined by a pre-selected cell surface marker or other marker.

As used herein, the term "purified population" of cells of interest refers to the cell population that has been isolated away from substantially all other cells that exist in their native environment, but also when the proportion of the cells of interest in a mixture of cells is greater than would be found in their native environment. For example, a purified population of cells represents an enriched population of the cells of interest, even if other cells and cell types are also present in the enriched population. In some embodiments, a purified population of cells represents at least about 10%, at least about 20%, at least about 30%, at least about 40%, at least about 50%, at least about 60%, at least about 70%, at least about 80%, at least about 90%, at least about 95%, at least about 99%, or about 100% of a mixed population of cells, with the proviso that the cells of interest comprise a greater percentage of the total cell population in the "purified" population than they did in the population prior to the purification.

As used herein, the term "population of cells" refers to a collection of more than one cell that is identical (clonal) or non-identical in phenotype and/or genotype.

As used herein, the term "cell colony" or "colony" refers to a grouping of closely associated cells formed as a result of cell growth. These terms are used irrelevantly to the number of cells constituting the colony.

As used herein, the term "dormant cells" is intended to encompass cells that are in a dormant or quiescent state which are required to be activated before they can undergo growth or differentiation.

As used herein, the term "dormant tiny cells" is intended to encompass cells that are in a dormant or quiescent state which are required to be activated before they can undergo growth and/or differentiation. The dormant tiny cells typically have a diameter less than 5 μm.

As used herein, the term "activation" of dormant cells refers to a measurable morphological, phenotypic, and/or functional change in the dormant state of the cells. Such activation is typically concurrent with the expression of specific markers for the activated cells. In one embodiment, activation is concurrent with a change in cell growth and/or development.

As used herein, the term "activated stem cells" is intended to encompass stem cells that are in an activated state and can undergo growth and/or differentiation under specific conditions.

As used herein, the term "composition" is intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume.

Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol. In certain embodiments, a composition includes a population of cells or a mixture of cells. In certain embodiments, the composition is formulated as a film, gel, patch, 3-D structure, or liquid solution.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier (or medium)", which may be used interchangeably with the term "biologically compatible carrier (or medium)", refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways. For topical use, the pharmaceutically acceptable carrier is suitable for manufacture of creams, ointments, jellies, gels, solutions, suspensions, etc. Such carriers are conventional in the art, e.g., for topical administration with polyethylene glycol (PEG). These formulations may optionally comprise additional pharmaceutically acceptable ingredients such as diluents, stabilizers, and/or adjuvants.

As used herein, the term "solution" refers to solutions, suspensions, emulsions, drops, ointments, liquid wash, sprays, and liposomes, which are well known in the art. In some embodiments, the liquid solution contains an aqueous pH buffering agent which resists changes in pH when small quantities of acid or base are added.

As used herein, the term "pH buffering agent" refers to an aqueous buffer solution which resists changes in pH when small quantities of acid or base are added to it. pH buffering solutions typically comprise a mixture of weak acid and its conjugate base, or vice versa. For example, pH buffering solutions may comprise phosphates such as sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate and dipotassium hydrogen phosphate; boric acid and borates such as, sodium borate and potassium borate; citric acid and citrates such as sodium citrate and disodium citrate; acetates such as sodium acetate and potassium acetate; carbonates such as sodium carbonate and sodium hydrogen carbonate, etc. pH adjusting agents can include, for example, acids such as hydrochloric acid, lactic acid, citric acid, phosphoric acid and acetic acid, and alkaline bases such as sodium hydroxide, potassium hydroxide, sodium carbonate and sodium hydrogen carbonate, etc. In some embodiments, the pH buffering agent is a phosphate buffered saline (PBS) solution (i.e., containing sodium phosphate, sodium chloride and in some formulations, potassium chloride and potassium phosphate).

As used herein, the term "formulated" or "formulation" refers to the process in which different substances, including one or more pharmaceutically active ingredients, are combined to produce a dosage form. In certain embodiments, two or more pharmaceutically active ingredients can be co-formulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "treating" refers to preventing, curing, reversing, attenuating, alleviating, minimizing, inhibiting, suppressing and/or halting one or more clinical symptoms of a disease or disorder prior to, during, and/or after an injury or intervention.

As used herein, the term "patient" or "subject" refers to animals, including mammals, such as murine, canine, equine, bovine, simian, or humans, who are treated with the pharmaceutical compositions or in accordance with the methods described herein.

As used herein, the term "delivery" refers to routes, approaches, formulations, technologies, and systems for transporting a pharmaceutical composition in the body as needed to safely achieve its desired therapeutic effect. The route of delivery can be any suitable route, including but not limited to, intravascular, intravenous, intraarterial, intramuscular, cutaneous, subcutaneous, percutaneous, intradermal, and intraepidermal routes. In some embodiments, an effective amount of the composition is formulated for applying on the skin or delivery into the skin of a patient. In some embodiments, an effective amount of the composition is formulated for delivery into the blood stream of a patient.

As used herein, the term "effective amount" refers to a concentration or amount of composition or a reagent, such as a composition as described herein, cell population or other agent, that is effective for producing an intended result, including cell growth and/or differentiation in vitro or in vivo, or for the treatment of a disease, disorder or condition in a patient in need thereof. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist and/or treating physician.

As used herein, the terms "effective period (or time)" and "effective conditions" refer to a period of time or other controllable conditions (e.g., temperature, humidity for in vitro methods), necessary or preferred for an agent or composition to achieve its intended result, e.g., the differentiation of cells to a pre-determined cell type.

As used herein, the term "control" or "control group" refers to an alternative subject or sample used in an experiment for comparison purpose. A control can be "positive" or "negative".

As used herein, the term "concurrently" refers to simultaneous (i.e., in conjunction) administration. In one embodiment, the administration is co-administration such that two or more pharmaceutically active ingredients, including any solid form thereof, are delivered together at one time.

As used herein, the term "sequentially" refers to separate (i.e., at different times) administration. In one embodiment, the administration is staggered such that two or more pharmaceutically active ingredients, including any solid form thereof, are delivered separately at different times.

As used herein, the term "target tissue" or "target organ" refers to an intended site for accumulation of the stem cells as disclosed herein and/or the differentiated cells derived from the stem cells as disclosed herein, following administration to a subject. For example, the methods as disclosed herein involve a target tissue or a target organ that has been damaged (e.g., by ischemia or other injury) in some embodiments.

As used herein, the terms "autologous transfer", "autologous transplantation", "autograft" and the like refer to treatments wherein the cell donor is also the recipient of the cell replacement therapy. The terms "allogeneic transfer", "allogeneic transplantation", "allograft" and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

As used herein, the term "ABCG2" or "ATP binding cassette (ABC) transporter G2" refers to a half transporter of the ABCG family belonging to the ABCG/white subfamily, and has the gene symbol ABCG2. ABCG2 is also known as MXR (Mitoxantrone Resistance protein, Miyake et al., 1999.), BCRP (Breast Cancer Resistance Protein, Doyle et al., 1998), or ABCP (placenta specific ABC transporter, Allikmets et al., 1998). The GENBANK® database discloses amino acid and nucleic acid sequences of ABCG2 from humans (e.g., AAG52982), mice (NM_011920.3), rats (BAC76396.1), cats (XP_019684813.1), dog (NP_001041486.1), pigs (NP_999175.1), cows (NP_001032555.2), and others.

As used herein, the term "CD34" refers to a cell surface marker found on certain hematopoietic and non-hematopoietic stem cells, and having the gene symbol CD34. The GENBANK® database discloses amino acid and nucleic acid sequences of CD34 from humans (e.g., AAB25223), mice (NP_598415), rats (XP_223083), cats (NP_001009318), pigs (MP_999251), cows (NP_776434), and others.

As used herein, the term "CD45" refers to a tyrosine phosphatase, also known as the leukocyte common antigen (LCA), and having the gene symbol PTPRC. This gene corresponds to GENBANK® Accession Nos. NP_002829 (human), NP_035340 (mouse), NP_612516 (rat), XP_002829 (dog), XP_599431 (cow), and AAR16420 (pig). The amino acid sequences of additional CD45 homologs are also present in the GENBANK® database, including those from several fish species and several non-human primates.

As used herein, the term "lineage markers" or "Lin" refers to characteristic molecules for cell lineages, e.g. cell surface markers, mRNAs, or internal proteins. Lineage-positive (Lin+) cells refer to a mix of cells expressing mature cell lineage markers. Lineage-negative (Lin−) cells include stem and progenitor cells, which are not differentiated mature cells. In one aspect, "Lin" refers to a panel of markers. The mouse lineage panel as used herein can react with cells from the major hematopoietic cell lineages, such as T lymphocytes, B lymphocytes, monocytes/macrophages, granulocytes, NK cells, and erythrocytes. As used herein, the FITC anti-mouse lineage antibody cocktail is designed for the flow cytometric identification of hematopoietic progenitors in mouse bone marrow. Components of the cocktail include anti-mouse CD3e, clone 145-2C11; anti-mouse Ly-6G/Ly-6C, clone RB6-8C5; anti-mouse CD11b, clone M1/70; anti-mouse CD45R/B220, clone RA3-6B2; anti-mouse TER-119/Erythroid cells, clone Ter-119. FITC anti-mouse lineage isotype control cocktail contains equivalent concentrations of isotype-matched negative control immunoglobulin.

As used herein, the term "keratin epithelium markers" refer to a panel of markers that include CK5, CK6, CK8.

2. Isolation of Dormant Tiny Cells

It is a surprising and expected discovery of the instant inventors that certain relatively small cells from the peripheral blood of mammalian subjects can be activated to become pluripotent stem cells. The pluripotency is demonstrated with the cells' ability to be differentiated into all three germ layers. Further, with a new activation and development system developed herein, the pluripotent stem cells can be expanded quickly and effectively in vitro. Moreover, the pluripotent stem cells derived from blood are not considered ethically and politically controversial, and do not require genetic manipulation. Yet another advantage of the present technology is that the pluripotent stem cells are demonstrated to be non-tumorigenic. Therefore, the presently disclosed technology will pave the way for practical cell-based therapy of tissue repair and regeneration and will also provide new therapeutics for unmet medical needs in chronic and aging related diseases.

In one embodiment, this disclosure provides a cell population enriched with cells that express CD45 and have a diameter of less than 5 μm. Such cells are herein referred to as "CD45+ cells" or "dormant tiny cells." In some embodiments, the composition or cell population includes a total of at least 100 cells, 1000 cells, 10,000 cells, or 100,000 cells, and at least about 50%, 60%, 70%, 75%, 80%, 85%, 90%, 95%, 98%, 99%, or 99.5% of them are dormant tiny cells. In some embodiments, all of the dormant tiny cells are obtained from a blood sample of a mammalian subject. In some embodiments, the composition further includes blood cells, such as red blood cells and white blood cells, at a relatively low percentage (e.g., less than about 30%, 25%, 20%, 15%, 10%, 9%, 8%, 7%, 6%, 5%, 4%, 3%, 2%, 1%, 0.5%, 0.2% or 0.1%).

In some embodiments, the dormant tiny cells in the composition include both intact and broken ones. In some embodiments, the ratio of the number of intact dormant tiny cells to the broken dormant tiny cells in the cell population is less than 1:1, at least about 1:1, 2:1, 3:1, 4:1, 5:1, 6:1, 7:1, 8:1, 9:1, 10:1, 11:1, 12:1, 13:1, 14:1, or 15:1.

In some embodiments, the dormant tiny cells have a diameter of about 2 µm, or alternatively about 2.5 µm, or alternatively about 3 µm, or alternatively about 3.5 µm, or alternatively about 4 µm, or alternatively about 4.5 µm, or alternatively about 5 µm, or alternatively between about 2-3 µm, or alternatively between about 2-4 µm, or alternatively between about 2-5 µm, or alternatively less than 5 µm, or alternatively less than 4 µm, or alternatively less than 3 µm. In some embodiments, the isolated dormant tiny cells have very high nucleus-cytoplasm ratio (v/v, also referred to as N:C ratio, or N/C). In some embodiments, the nucleus-cytoplasm ratio of a dormant tiny cell as disclosed herein may be at least 9:1, or alternatively at least 8:1, or alternatively at least 7:1, or alternatively at least 6:1, or alternatively at least 5:1. When seeded in regular cell culture medium (e.g., α-MEM with 20% FBS) in vitro, in some embodiments, the dormant tiny cells do not proliferate and become senescent in a few days. In some embodiments, the isolated population of dormant tiny cells express both markers CD34 and CD45, and do not express the marker ABCG2. In some embodiments, the dormant tiny cells are further characterized to be Lin−.

The dormant tiny cells, in some embodiments, may have high ratio of small RNA (sRNA, including micro RNA) to ribosomal RNA (rRNA). In some embodiments, the ratio of small RNA to ribosomal RNA is at least 22:1, or alternatively at least 20:1, or alternatively at least 18:1, or alternatively at least 15:1, or alternatively at least 12:1, or alternatively at least 10:1, or alternatively at least 9:1, or alternatively at least 8:1, or alternatively at least 7:1, or alternatively at least 6:1, or alternatively at least 5:1. Low level or minimum expression of mitochondrial marker (e.g., COX IV), endoplasmic reticulum (ER) marker (e.g., Calnexin), and ribosome marker (e.g., RPS3) may also indicate that the isolated population of stem cells are in a dormant/quiescent state, in some aspects.

The dormant tiny cells may be analyzed using the cell surface markers and intracellular markers such as those shown in Table 1, below.

TABLE 1

| Antigen or Marker | Example GenBank Accession No. |
| --- | --- |
| CD34 | NM_001111059 |
| CD45 | NM_011210.4 |
| CD44 | NM_009851 |
| CD150 | NM_013730.4 |
| CD90.1 (Thy1.1) | AY445633.1 |
| CD105 | NM_007932.2 |
| CD133 | NM_008935.2 |
| Sca1(Ly6a) | NM_010738 |
| c-kit (CD 117) | NM_001122733.1 |
| Oct4 (Oct3/4, Pou5f1) | BC068268.1 |
| SSEA1 | NM_010242.3 |
| Nanog | AY278951.1 |
| Vasa | NM_001145885 |

In some embodiments, the isolated dormant tiny cells express one or more early stage stem cell markers (e.g., Oct4, Nanog, SSEA1, Vasa). In some embodiments, the dormant tiny cells express one or more markers of the group of hematopoietic markers (e.g., CD34, CD45, CD133, CD150), and MSC markers (e.g., CD44, CD105, Sca1, CD90.1). In some embodiments, the isolated population of dormant tiny cells express one or more of the markers identified in Table 1. In one aspect, two of the markers identified in Table 1 are present, or alternatively three, or alternatively four, or alternatively five, and increasing up to the presence of all markers. In some embodiments, the dormant tiny cells do not express E-cadherin, CD184, and/or CD41.

In some embodiments, provided is a method of isolating dormant tiny cells as disclosed herein from a blood sample. The dormant tiny cells can be isolated from the periphery blood by any means that allows for isolation of cells. For example, the methods as disclosed herein may include removing at least a portion of the blood cells and platelet from the blood sample, and centrifuging the sample to obtain the pellet that includes the dormant tiny cells. In other aspects, the methods may include cell sorting and cell isolation methods based on one or more identifying markers. For example, fluorescence-activated cell sorting (FACS) or magnetic-activated cell sorting (MACS) may be used to sort and isolate the dormant tiny cells. In some embodiments, other methods can be used to isolate the dormant tiny cells as disclosed herein. Examples of some isolation procedures are provided in EXAMPLE 1, infra.

In one aspect, the method of isolation of dormant tiny cells comprises (1) removing at least a portion of red blood cells from a blood sample; (2) removing at least a portion of platelets from the sample; (3) centrifuging the sample at 400×g-3000×g, and (4) obtaining a pellet that comprises the dormant tiny cells as disclosed herein. In some aspects, the sample in step (3) may be centrifuged at about 400×g, or alternatively at about 500×g, or alternatively at about 800×g, or alternatively at about 1000×g, or alternatively at about 1200×g, or alternatively at about 1500×g, or alternatively at about 1800×g, or alternatively at about 2000×g, or alternatively at about 2200×g, or alternatively at about 2500×g, or alternatively at about 2800×g, or alternatively at about 3000×g, or alternatively at about 3500×g, or alternatively at about 4000×g, or alternatively at about 4500×g, or alternatively at about 5000×g, or alternatively at about 5500×g, or alternatively at about 6000×g, or alternatively at about 6500×g, or alternatively at about 7000×g, or alternatively at about 7500×g, or alternatively at about 8000×g, or alternatively at about 9000×g, or alternatively at about 10,000×g, or alternatively at above 10,000×g.

In some embodiments, provided are methods of isolating a specific enriched population of stem cells based on the specific marker(s) of the stem cells. For example, the methods may be used to isolate a cell population enriched in CD34+/CD45+/ABCG2−/Lin− cells (e.g., by FACS or MACS). In another example, the methods may be used to isolate a cell population enriched in CD34+/ABCG2− cells. In other embodiments, the methods may be used to isolate a cell population enriched in cells having a certain combination of specific markers (e.g., the markers for identifying dormant tiny cells as disclosed herein).

In some embodiments, the dormant tiny cells may be isolated from other sources/tissues so long as the tissue contains viable dormant tiny cells as disclosed herein. In some embodiments, the dormant tiny cells may be isolated from a subject at any age. In some embodiments, the dormant tiny cells may be isolated from a subject at any time. In some embodiments, the dormant tiny cells can be isolated from animals such as, but not limited to, equine, canine, porcine, bovine, murine, simian, and human.

3. Activation and Development

To activate and culture the isolated population of dormant tiny cells in vitro, an activation/development system has been established. In some embodiments, the activation/development system includes one or more cell types/cell lines selected from primary hepatocytes, human hepatoblastoma (HepG2) cells, hepatocyte cell line, and mouse embryo fibroblast (MEF) cell line. Non-limiting examples of the hepatocyte cell line include AML12 and HepaRG. In some embodiments, the activation/development system may include other types of hepatoblastoma cells and/or other types of embryo fibroblast cell lines. In some embodiments, the activation/development system may include other types of cells and/or cell lines. In some aspects, the activation/development system may include at least one, or alternatively at least two, or alternatively at least three, or alternatively at least four of the above-mentioned cells/cell lines.

In one aspect, the activation/development system includes a cell mixture of at least primary hepatocytes, HepG2 cells, hepatocyte cell line, and MEF cell line. In another aspect, the activation/development system includes a cell mixture of at least primary hepatocytes, HepG2 cells, and hepatocyte cell line. In another aspect, the activation/development system includes a cell mixture of at least primary hepatocytes, HepG2 cells, and MEF cell line. In another aspect, the activation/development system includes a cell mixture of at least primary hepatocytes, hepatocyte cell line, and MEF cell line. In another aspect, the activation/development system includes a cell mixture of at least HepG2 cells, hepatocyte cell line, and MEF cell line. In another aspect, the activation/development system includes a cell mixture of at least primary hepatocytes and HepG2 cells. In another aspect, the activation/development system includes a cell mixture of at least primary hepatocytes and hepatocyte cell line. In another aspect, the activation/development system includes a cell mixture of at least primary hepatocytes and MEF cell line. In another aspect, the activation/development system includes a cell mixture of at least HepG2 cells and hepatocyte cell line. In another aspect, the activation/development system includes a cell mixture of at least HepG2 cells and MEF cell line. In another aspect, the activation/development system includes a cell mixture of at least hepatocyte cell line and MEF cell line. In another aspect, the activation/development system includes at least primary hepatocytes. In another aspect, the activation/development system includes at least HepG2 cells. In another aspect, the activation/development system includes at least hepatocyte cell line. In another aspect, the activation/development system includes at least MEF cell line.

In one embodiment, provided herein is a method of activating and culturing the dormant tiny cells in vitro. In some embodiments, the dormant tiny cells may be cocultured with the cells or cell mixture as disclosed herein using Transwell plates. For example, cells or a cell mixture of the above-mentioned cells/cell lines can be prepared and treated with Mitomycin C to mitotically inactivate the cells. Then the cells/cell mixture can be seeded on the bottom of cell culture plates in a coculture medium. The isolated population of dormant tiny cells can be seeded on the Transwell membranes to be cocultured with the cells/cell mixture. The coculture medium may include α-MEM medium with 5-50% of FBS (fetal bovine serum). For example, the coculture medium may include α-MEM medium with about 5%, or alternatively about 10%, or alternatively about 15%, or alternatively about 20%, or alternatively about 25%, or alternatively about 30%, or alternatively about 35%, or alternatively about 40%, or alternatively about 45%, or alternatively about 50% of FBS. In some embodiments, other culture medium may be used in the methods as disclosed herein. Optionally other reagents and factors may be added to the coculture medium.

In another aspect, provided herein is a method of activating and culturing the dormant tiny cells using conditioned medium. In some aspects, the culture medium may be conditioned with the above-mentioned cells or mixture of cells/cell lines before use in the activation/development system. For example, the above-mentioned cells/cell mixture can be suspended in cell culture medium and then seeded in a cell culture dish/plate. The cell culture medium for culturing the cells/cell mixture may include DMEM with 5-50% of FBS. For example, the medium may include DMEM with about 5%, or alternatively about 10%, or alternatively about 15%, or alternatively about 20%, or alternatively about 25%, or alternatively about 30%, or alternatively about 35%, or alternatively about 40%, or alternatively about 45%, or alternatively about 50% of FBS. In some embodiments, other culture medium may be used in the methods as disclosed herein. Optionally other reagents and factors may be added to the medium. The conditioned medium can be collected from the cell culture dishes/plates, and the remaining cells in the medium can be removed (e.g., via centrifugation and/or filtering) before use of the medium to culture the isolated dormant tiny cells. The collected conditioned medium may be mixed with the above-mentioned coculture medium, for culturing the dormant tiny cells. For example, based on the total volume of the medium mixture, the conditioned medium as disclosed herein may be about 5% (v/v), or alternatively about 10%, or alternatively about 15%, or alternatively about 20%, or alternatively about 25%, or alternatively about 30%, or alternatively about 35%, or alternatively about 40%, or alternatively about 45%, or alternatively about 50%, or alternatively about 55%, or alternatively about 60%, or alternatively about 65%, or alternatively about 70%, or alternatively about 75%, or alternatively about 80%, or alternatively about 85%, or alternatively about 90%, or alternatively about 95%. Optionally other reagents and factors may be added to the mixture of medium.

Embodiments of the disclosure also provide a population of activated stem cells derived from the dormant tiny cells as disclosed herein. The activated stem cells may be obtained by culturing the dormant tiny cells in the above-mentioned activation/development system for an effective period of time. In some aspects, the culturing time effective for activating the dormant tiny cells may include, but not limited to, at least 1 hour, or alternatively at least 2 hours, or alternatively at least 4 hours, or alternatively at least 12 hours, or alternatively at least 1 day, or alternatively at least 2 days, or alternatively at least 3 days, or alternatively at least 4 days, or alternatively at least 5 days, or alternatively at least 8 days, or alternatively at least 10 days, or alternatively at least 12 days, or alternatively at least 15 days, or alternatively at least 18 days, or alternatively at least 20 days. The cell culture medium may be changed every 1 day, or alternatively every 2 days, or alternatively every 3 days, or alternatively every 4 days, or alternatively every 5 or more days. In some embodiments, the activated stem cells may be obtained by culturing the dormant tiny cells in other culture systems, culture medium, or conditions for an effective period of time. In some embodiments, the activated stem cells are characterized as a highly heterogeneous cell mixture, including various sub-populations of cells characterized by different sets of markers.

In some embodiments, other cell culture mediums and/or cell culture conditions may be used to activate and/or culture the stem cells as disclosed herein. In some embodiments, the cell culture medium and/or cell culture conditions used in the activation/development system as disclosed herein may be used to culture other types of cells and/or other types of stem cells. For example, the cell culture medium and/or cell culture conditions used in the activation/develop system may be used to culture one or more of cells selected from the group consisting of embryonic stem (ES) cells, hematopoietic stem cells (HSCs), mesenchymal stem cells (MSCs), endothelial stem cells (ESCs), mammary stem cells (MaSCs), intestinal stem cells (ISCs), neural stem cells (NSCs), adult olfactory stem cells (OSCs), neural crest stem cells (NCSCs), and testicular stem cells (TSCs), and induced pluripotent stem cells (iPSCs).

In some embodiments, the activated stem cells express ABCG2, which is not expressed in the dormant tiny cells. In some aspects, a nucleic acid stain (e.g., Hoechst 33342) gradually diffuses outside of the activated stem cells cultured in the activation/development system, while the nucleic acid stain in the dormant tiny cells does not diffuse in a regular cultured medium as disclosed herein. In some embodiments, the ratio of small RNA to ribosomal RNA, which is high in the dormant tiny cells, decreases significantly after activation of the stem cells. In some embodiments, the activated stem cells may have a ratio of small RNA to ribosomal RNA that is below 1:4, or alternatively below 1:5, or alternatively below 1:6, or alternatively below 1:7, or alternatively below 1:8, or alternatively below 1:9, or alternatively below 1:10. In some embodiments, the activated stem cells may have substantially increased levels of COX IV, RPS3, and Calnexin, compared to the dormant tiny cells.

Also provided herein, in some embodiments, is a population of activated stem cells that are $ABCG2^+$, which can be further characterized into several sub-populations that are $CD34^+/CD45^+$, $CD34^+/CD45^-$, $CD34^-/CD45^+$, and/or $CD34^-/CD45^-$. In one embodiment, at least about 50%, or alternatively at least about 55%, or alternatively at least about 60%, or alternatively at least about 66%, or alternatively at least about 70%, or alternatively at least about 75%, or alternatively at least about 80%, or alternatively at least about 85%, or alternatively at least about 90%, or alternatively at least about 95%, or alternatively at least about 99% of the population of activated stem cells are $CD34^+/CD45^-$. In one aspect, less than 50%, or alternatively less than 45%, or alternatively less than 40%, or alternatively less than 35%, or alternatively less than 30%, or alternatively less than 25%, or alternatively less than 20%, or alternatively less than 15%, or alternatively less than 10%, or alternatively less than 5%, or alternatively less than 2%, or alternatively less than 1%, or alternatively less than 0.5% of the activated stem cells are $CD34^+/CD45^+$, $CD34^-/CD45^+$, $CD34^-/CD45^-$, or any combination thereof.

In some embodiments, one or more of the sub-populations of the activated stem cells as disclosed herein can expand quickly in the activation/development system in vitro. In some embodiments, the doubling time for the sub-populations of the activated stem cells may vary. In some embodiments, the doubling time for one or more of the sub-populations of the activated stem cells in the activation/development system may be more than 50 hours, or alternatively less than 50 hours, or alternatively less than 45 hours, or alternatively less than 40 hours, or alternatively less than 35 hours, or alternatively less than 30 hours, or alternatively less than 25 hours, or alternatively between about 20 and about 50 hours, or alternatively between about 20 and about 40 hours, or alternatively between about 20 and about 30 hours. In some embodiments, one or more of the sub-populations of the activated stem cells can expand in other cell culture systems and/or under other culture conditions in vitro.

Also provided herein are methods for purifying a sub-population of activated stem cells derived from the dormant tiny cells as disclosed herein. In one aspect, provided is a method for purifying a sub-population of $CD34^+/CD45^+$ activated stem cells derived from the dormant tiny cells as disclosed herein. In one aspect, provided is a method for purifying a sub-population of $CD34^+/CD45^-$ activated stem cells derived from the dormant tiny cells as disclosed herein. In one aspect, provided is a method for purifying a sub-population of $CD34^-/CD45^+$ activated stem cells derived from the dormant tiny cells as disclosed herein. In one aspect, provided is a method for purifying a sub-population of $CD34^-/CD45^-$ activated stem cells derived from the dormant tiny cells as disclosed herein. In one aspect, provided is a method for purifying a sub-population of $CD34^+$ activated stem cells derived from the dormant tiny cells as disclosed herein. In one aspect, provided is a method for purifying a sub-population of $CD34^-$ activated stem cells derived from the dormant tiny cells as disclosed herein. In one aspect, provided is a method for purifying a sub-population of $CD45^+$ activated stem cells derived from the dormant tiny cells as disclosed herein. In one aspect, provided is a method for purifying a sub-population of $CD45^-$ activated stem cells derived from the dormant tiny cells as disclosed herein. In one aspect, provided is a method for purifying a sub-population of activated stem cells that has a certain set of markers, derived from the dormant tiny cells as disclosed herein.

In one embodiment, after culturing in the activation/development system for a period of time (e.g., 10-20 days), one or more cell colonies are developed. The dormant tiny cells cultured in regular medium (e.g., $\alpha$-MEM medium with 20% FBS) do not grow and expand, and do not develop into cell colonies, in some aspects.

In some embodiments, provided herein are methods for isolating a cell colony derived from the dormant tiny cells as disclosed herein. For example, a cell colony can be picked up using a cloning cylinder. Alternatively, a cell colony can be isolated by trypsinizing and detaching the colony from the cell culture plate/dish. It should be understood that other methods can also be employed to isolate the cell colonies. It is identified (e.g., by FACS) that at least 60%, or alternatively at least 70%, or alternatively at least 80%, or alternatively at least 95%, or alternatively at least 99% of the stem cells in the isolated stem cell colonies are $CD34^+/CD45^-$. In one aspect, at least 90% of the stem cells in the isolated stem cell colonies are $CD34^+/CD45^-$.

Also provided herein are methods for purifying a population of activated stem cells from the isolated colonies as disclosed herein. In one aspect, at least about 60%, or alternatively at least about 70%, or alternatively at least about 80%, or alternatively at least about 90%, or alternatively at least about 95%, or alternatively at least about 99%, or alternatively at least about 99.9% of the cells in the isolated stem cell colonies are $CD34^+/CD45^-$. In some embodiments, the cells in the colonies may include, in addition to the $CD34^+/CD45^-$ cells, sub-populations of cells that may be $CD34^+/CD45^+$, $CD34^-/CD45^+$, and/or $CD34^-/CD45^-$. In one aspect, less than about 40%, or alternatively less than about 30%, or alternatively less than about 20%, or alternatively less than about 10%, or alternatively less than about 5%, or alternatively less than about 2%, or alternatively less than about 1% of the cells in the isolated stem cell colonies are $CD34^+/CD45^+$, $CD34^-/CD45^+$, $CD34^-/CD45^-$, or of any combination thereof. In some embodiments, based on total numbers of cells, less than about 40%, or alternatively less than about 30%, or alternatively less than about 20%, or alternatively less than about 10%, or alternatively less than about 5%, or alternatively less than about 2%, or alternatively less than about 1%, or alternatively less than about 0.1% of the purified cell population are not CD34$^+$/CD45$^-$. In some embodiments, methods such as MACS or FACS can be used to purify a specific population or an enriched cell population from the activated stem cells. In some embodiments, other methods can be used to purify a specific population or an enriched cell population from the activated stem cells.

Figure 6:
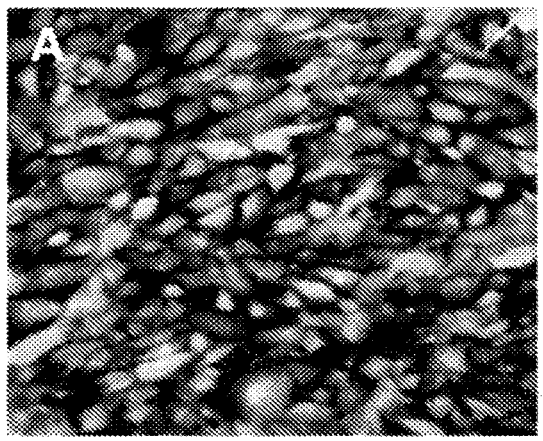
FIG. 6 is an illustration showing in vitro cell culture of a purified population of $CD34^+/CD45^-$ stem cells from the stem cell colonies.
Figure 6:
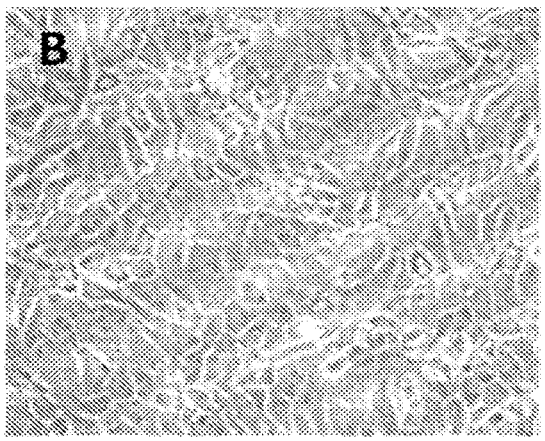
Figure 6:
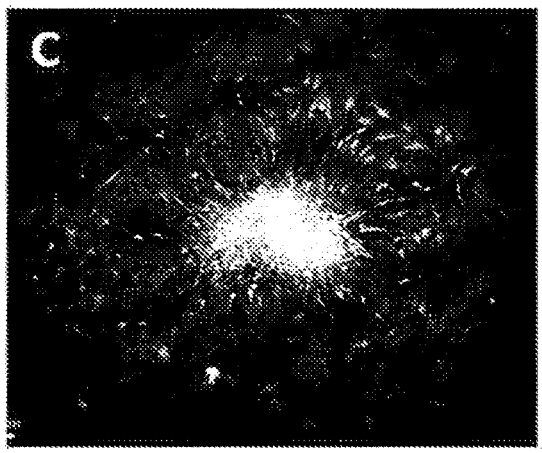
Figure 6:
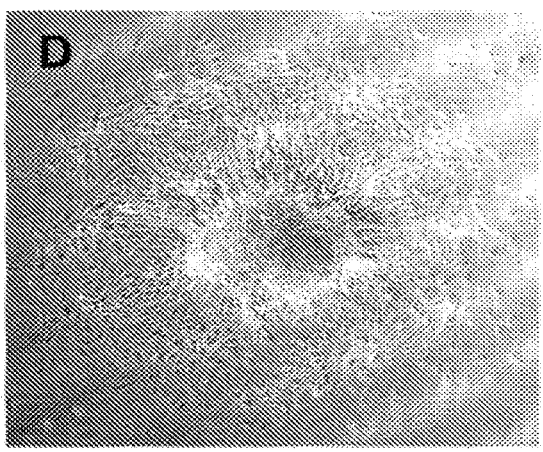

In some embodiments, a single cell dilution of the activated stem cells can be performed and then cultured in the activation/development system as disclosed herein. After a period of time (e.g., about 10-20 days), one or more colonies derived from single cells can be developed. The cell colony derived from single cells has an embryoid body-like (EB-like) structure (FIG. 6, D). In one aspect, substantially 100% of the cells in the single cell colony are CD34$^+$/CD45$^-$. In one aspect, at least about 90%, or alternatively at least about 95%, or alternatively at least about 99%, or alternatively at least about 99.9% of the cells in the single cell colony are CD34$^+$/CD45$^-$.

Also provided herein are methods for purifying the CD34$^+$/CD45$^-$ stem cell population from the isolated cell colonies or single cell colony as disclosed herein. In one embodiment, the CD34$^+$/CD45$^-$ stem cell population can be purified using, e.g., MACS or FACS. The purification methods are provided in Example 2, infra. It should be understood that other methods can also be employed to purify CD34$^+$/CD45$^-$ stem cell population from the cell colonies. In some embodiments, the methods disclosed herein or other methods can be used to purify other cell populations from the colonies.

The purified CD34$^+$/CD45$^-$ stem cells have a diameter of about 20-30 μm, larger than the dormant tiny cells. For example, a purified CD34$^+$/CD45$^-$ stem cell may have a diameter of less than 20 μm, or alternatively about 20 μm, or alternatively about 22 μm, or alternatively about 24 μm, or alternatively about 26 μm, or alternatively about 28 μm, or alternatively about m, or alternatively more than 30 m. The purified CD34$^+$/CD45$^-$ stem cells are further characterized with relatively high nucleus-cytoplasm ratio of about 5:1, or alternatively about 6:1, or alternatively about 7:1, or alternatively about 8:1, or alternatively about 9:1. In one aspect, the nucleus of a purified CD34$^+$/CD45$^-$ stem cell is at least about 50%, or alternatively at least about 60%, or alternatively at least about 70%, or alternatively at least about 80%, or alternatively at least about 90% of the total cell volume. The purified CD34$^+$/CD45$^-$ stem cells can expand quickly in vitro (e.g., at about 26 hours doubling time) in regular cell culture medium (e.g., α-MEM with 20% FBS). In other aspects, the doubling time of the purified CD34$^+$/CD45$^-$ stem cells may vary in other culture conditions. In some aspects, the purified CD34$^+$/CD45$^-$ stem cells may be cultured in vitro as adherent cell culture and/or as suspension cell culture. When the purified CD34$^+$/CD45$^-$ stem cells adhere to the cell culture dishes/plates and reach confluency, the cell arrangement resembles epithelial cell culture (FIGS. 6, A and B).

In one aspect, the purified CD34$^+$/CD45$^-$ stem cells are further analyzed by markers as listed in Table 2, as below. In some embodiments, the purified CD34$^+$/CD45$^-$ stem cells express one or more of the markers identified in Table 2. In one aspect, two of the markers identified in Table 2 are present, or alternatively three, or alternatively four, or alternatively five, and increasing up to the presence of all markers. Other confirmatory antigens are exemplified in Table 2 and described below.

TABLE 2

| Antigen or Marker | Example GenBank Accession No. |
| --- | --- |
| CD34 | NM_001111059 |
| CD14 | NM_009841.4 |
| CD19 | NM_009844.2 |
| CD117 | NM_001122733.1 |
| CD29 | NM_010578.2 |
| CD44 | NM_009851 |
| CD73 | L12059.1 |
| CD90.1 (Thy1.1) | AY445633.1 |
| CD31 | NM_008816.3 |
| CD105 | NM_007932.2 |
| CD106 | NM_011693.3 |
| CD133 | NM_008935.2 |
| CD184 | NM_009911.3 |
| Sca1(Ly6a) | NM_010738 |
| Oct4 (Oct3/4, Pou5f1) | BC068268.1 |
| SSEA1 | NM_010242.3 |
| Sox2 | AB044284.1 |
| Nanog | AY278951.1 |
| Vasa | NM_001145885 |
| Keratin epithelium | (See above) |
| CK18 | NM_010664.2 |
| CK19 | M28698.1 |
| Nestin | NM_016701.3 |
| Osteocalcin (BGLAP) | NM_007541.3 |
| ABCG2 | NM_011920.3 |

In some aspects, the purified CD34$^+$/CD45$^-$ stem cells may express one or more markers of the group of early stage markers (e.g., Oct4, Sox2, Nanog, Vasa, SSEA1), hematopoietic markers (e.g., CD34, CD14, CD19, CD117), MSC markers (e.g., CD44, CD73, Thy1.1 (CD90.1), CD105, CD106, Sca1), epithelium markers (e.g., keratin epithelium, CK18, CK19), neural stem cell markers (e.g., Nestin), osteoblast markers (e.g., Osteocalcin), endothelium markers (e.g., CD31), cell migration markers (e.g., CD184), cell integrin markers (e.g., CD29), multi-types stem cell (e.g., neuron, HSC, endothelium) markers (e.g., CD133).

In some embodiments, the purified CD34$^+$/CD45$^-$ stem cell population express one or more markers of Oct4, Nanog, ABCG2, CD117, CD29, CD44, CD73, CD90.1, CD105, Sca1, CD31, CD184, Keratin epithelium, Nestin, and Osteocalcin. In one aspect, two of the markers, or alternatively three, or alternatively four, or alternatively five, and increasing up to all of markers Oct4, Nanog, ABCG2, CD117, CD29, CD44, CD73, CD90.1, CD105, Sca1, CD31, CD184, Keratin epithelium, Nestin, and Osteocalcin are present. In one aspect, the purified CD34$^+$/CD45$^-$ stem cells express at least ABCG2, Oct4, Nanog, CD117, CD29, CD44, Sca1, CD31, CD184, CD133, Keratin epithelium, Nestin, and Osteocalcin. In one aspect, the purified CD34$^+$/CD45$^-$ stem cells express at least ABCG2, Oct4, Sox2, CD19, CD29, CD90, CD31, CD184, CK18, Nestin, and Osteocalcin. In one aspect, the purified CD34$^+$/CD45$^-$ stem cells express at least ABCG2, SSEA1, CD14, CD29, CD105, CD31, CD184, CK19, Nestin, and Osteocalcin. In one aspect, the purified CD34$^+$/CD45$^-$ stem cells express at least ABCG2, Nanog, CD117, CD29, CD90, CD31, CD184, Keratin epithelium, Nestin, and Osteocalcin. In one aspect, the purified CD34$^+$/CD45$^-$ stem cells express at least ABCG2, Nanog, CD117, CD90, CD31, CD133, Nestin, and Osteocalcin.

In some embodiments, the purified CD34$^+$/CD45$^-$ stem cells are further characterized as Lin$^-$. In some embodiments, the purified CD34$^+$/CD45$^-$ stem cells are identified to be negative in one or more of CD3, CD4, CD8a, CD11b, CD13, CD45, Lin, and CD140a. In some embodiments, the purified CD34$^+$/CD45$^-$ stem cells do not express at least one, or alternatively at least two, or alternatively at least three, or alternatively at least four, or alternatively at least five, or increasing up to all of CD3, CD4, CD8a, CD11b, CD13, CD45, Lin, and CD140a.

The expression of early embryonic stage markers (e.g., Oct4, Sox2, Nanog, Vasa, SSEA1) indicates that the purified CD34$^+$/CD45$^-$ stem cells are at early stage. Expression of keratin epithelium markers is also observed in the purified CD34$^+$/CD45$^-$ stem cells. It is know that the keratin epithelium markers are expressed in the epiblast cells at early embryonic stage, but are not expressed in adult blood cells.

4. Differentiation of the Activated Stem Cells

The purified CD34$^+$/CD45$^-$ stem cell population can also be identified by their pluripotency, e.g., the capacity to differentiate into cell types from all three germ layers (ectoderm, mesoderm, and endoderm) using the appropriate culture conditions and medium. Confirmation of the differentiation state of the cells can be performed by identification of cell type specific markers as known to those of skill in the art.

The present disclosure provides methods for inducing differentiation of the purified CD34$^+$/CD45$^-$ stem cell population into ectodermal lineage. Also provided are compositions or populations of differentiated cells in ectodermal lineage, derived from the purified CD34$^+$/CD45$^-$ stem cell population. In one aspect, the purified CD34$^+$/CD45$^-$ stem cells are capable of differentiation into at least one of the cell types in the ectodermal lineage. For example, the purified CD34$^+$/CD45$^-$ stem cells are capable of differentiation into neural cells and epithelial cells. In another aspect, the purified CD34$^+$/CD45$^-$ stem cells are capable of differentiation into at least two, at least three, and increasing up to all of the cell types in the ectodermal lineage. Non-limiting examples of cells that differentiate into ectodermal lineage include, but are not limited to epithelial cells, neurogenic cells, and neurogliagenic cells.

In other aspects, also provided are methods of inducing differentiation of the activated stem cell population, derived from the dormant tiny cells as disclosed herein, into ectodermal lineage. Also provided are compositions or populations of differentiated cells in ectodermal lineage, derived from the activated stem cell population that are derived from the dormant tiny cells as disclosed herein. In other aspects, also provided are methods of inducing differentiation of various sub-populations in the activated stem cell population, which are derived from the dormant tiny cells as disclosed herein, into ectodermal lineage. Also provided are compositions or populations of differentiated cells in ectodermal lineage, derived from various sub-populations in the activated stem cell population, derived from the dormant tiny cells as disclosed herein. In other aspects, also provided are methods of inducing differentiation of the sub-populations of the activated stem cells as disclosed herein into ectodermal lineage. Also provided are compositions or populations of differentiated cells in ectodermal lineage, derived from the sub-populations of the activated stem cells as disclosed herein.

The present disclosure provides methods for inducing differentiation of the purified CD34$^+$/CD45$^-$ stem cell population into mesodermal lineage. Also provided are compositions or populations of differentiated cells in mesodermal lineage, derived from the purified CD34$^+$/CD45$^-$ stem cell population. In another aspect, the purified CD34$^+$/CD45$^-$ stem cells are capable of differentiation into at least one of the cell types in the mesodermal lineage. For example, the purified CD34$^+$/CD45$^-$ stem cells are capable of differentiation into cardiomyocytes and osteoblasts. In another aspect, the purified CD34$^+$/CD45$^-$ stem cells are capable of differentiation into at least two, or alternatively at least three, or alternatively at least four, and increasing up to all of the cell types in the mesodermal lineage. Non-limiting examples of cells that differentiate into mesodermal lineage include, but are not limited to adipogenic, leiomyogenic, chondrogenic, cardiogenic, dermatogenic, hematopoetic, hemangiogenic, myogenic, nephrogenic, urogenitogenic, osteogenic, pericardiogenic, or stromal cells.

In other aspects, also provided are methods of inducing differentiation of the activated stem cell population, which are derived from the dormant tiny cells as disclosed herein, into mesodermal lineage. Also provided are compositions or populations of differentiated cells in mesodermal lineage, derived from the activated stem cell population that is derived from the dormant tiny cells as disclosed herein. In other aspects, also provided are methods of inducing differentiation of various sub-populations in the activated stem cell population, which are derived from the dormant tiny cells as disclosed herein, into mesodermal lineage. Also provided are compositions or populations of differentiated cells in mesodermal lineage, derived from various sub-populations in the activated stem cell population, derived from the dormant tiny cells as disclosed herein. In other aspects, also provided are methods of inducing differentiation of the sub-populations of the activated stem cells as disclosed herein into mesodermal lineage. Also provided are compositions or populations of differentiated cells in mesodermal lineage, derived from the sub-populations of the activated stem cells as disclosed herein.

The present disclosure provides methods for inducing differentiation of the purified CD34$^+$/CD45$^-$ stem cell population into endodermal lineage. Also provided are compositions or populations of differentiated cells in endodermal lineage, derived from the purified CD34$^+$/CD45$^-$ stem cell population. In one aspect, the purified CD34$^+$/CD45$^-$ stem cells are capable of differentiation into at least one of the cell types in the endodermal lineage. For example, the purified CD34$^+$/CD45$^-$ stem cells are capable of differentiation into hepatocytes. In another aspect, the purified CD34$^+$/CD45$^-$ stem cells are capable of differentiation into at least two, or alternatively at least three, or alternatively at least four, or alternatively at least five, and increasing up to all of the cell types in the endodermal lineage. Non-limiting examples of cells that differentiate into endodermal lineage include, but are not limited to cells in the pancreas, liver, lung, stomach, intestine, and thyroid.

In other aspects, also provided are methods of inducing differentiation of the activated stem cell population, derived from the dormant tiny cells as disclosed herein, into endodermal lineage. Also provided are compositions or populations of differentiated cells in endodermal lineage, derived from the activated stem cell population derived from the dormant tiny cells as disclosed herein. In other aspects, also provided are methods of inducing differentiation of various sub-populations in the activated stem cell population, derived from the dormant tiny cells as disclosed herein, into endodermal lineage. Also provided are compositions or populations of differentiated cells in endodermal lineage, derived from various sub-populations in the activated stem cell population, derived from the dormant tiny cells as disclosed herein. In other aspects, also provided are methods of inducing differentiation of the sub-populations of the activated stem cells as disclosed herein into endodermal lineage. Also provided are compositions or populations of differentiated cells in endodermal lineage, derived from the sub-populations of the activated stem cells as disclosed herein.

5. Method of Use

The present disclosure provides methods of treating diseases in a subject in need thereof using the activated stem cells as disclosed herein. In some embodiments, provided are methods of treating diseases in a subject in need thereof using differentiated cells derived from the activated stem cells as disclosed herein. Regenerative medicine includes therapies designed to aid the repair, replacement, or regeneration of damaged cells, tissues, or organs. The methods as disclosed herein may be used in cell-based therapies in the generative medicine.

In some aspects, the methods and compositions disclosed herein may be used to treat diseases or conditions such as degenerative diseases, proliferative disorders, hereditary diseases, injuries, and/or organ failures. Non-limiting examples of the diseases or conditions include neurodegenerative disorders; neurological disorders such as cognitive impairment, and mood disorders; auditory disease such as deafness; osteoporosis; cardiovascular diseases; diabetes; metabolic disorders; respiratory diseases; drug sensitivity conditions; eye diseases such as macular degeneration; immunological disorders; hematological diseases; kidney diseases; proliferative disorders; genetic disorders, traumatic injury, stroke, organ failure, or loss of limb. Other examples of the diseases include a neurodegenerative disorder, a neurological disorder, an eye disease, a mood disorder, a respiratory disease, an auditory disease, a cardiovascular disease, an immunological disorder, a hematological disease, a metabolic disorder, a kidney disease, a proliferative disorder, a genetic disorder, an autoimmune disease, a drug sensitivity condition, a cognitive impairment, depression, deafness, osteoporosis, diabetes, macular degeneration, obesity, Alexander's disease, Alper's disease, Alzheimer's disease, amyotrophic lateral sclerosis, ataxia telangiectasia, Batten disease, Canavan disease, Cockayne syndrome, corticobasal degeneration, Creutzfeldt-Jakob disease, Huntington's disease, HIV-associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, a prion disease, Refsum's disease, Sandhoffs disease, Schilder's disease, subacute combined degeneration of spinal cord secondary to pernicious anaemia, schizophrenia, spinocerebellar ataxia, spinal muscular atrophy (SMA), Steele-Richardson-Olszewski disease, tabes dorsalis, acquired immune deficiency, leukemia, lymphoma, a hypersensitivity (allergy), severe combined immune deficiency, acute disseminated encephalomyelitis, addison's disease, ankylosing spondylitis, antiphospholipid antibody syndrome, autoimmune hemolytic anemia, autoimmune hepatitis, bullous pemphigoid, coeliac disease, dermatomyositis, diabetes mellitus type 1, diabetes mellitus type 2, Goodpasture's syndrome, Graves' disease, Guillain-Barre syndrome, Hashimoto's disease, idiopathic thrombocytopenic purpura, lupus erythematosus, myasthenia gravis, pemphigus, pernicious anaemia, polymyositis, primary biliary cirrhosis, rheumatoid arthritis, Sjogren's syndrome, temporal arthritis, vasculitis, Wegener's granulomatosis, aneurysm, angina, arrhythmia, atherosclerosis, cardiomyopathy, calcific aortic valve disease (CAVD), cerebrovascular accident (stroke), cerebrovascular disease, congenital heart disease, congestive heart failure, myocarditis, valve disease coronary, cardiomyopathy, diastolic dysfunction, endocarditis, hypertension, hypertrophic cardiomyopathy, mitral valve prolapse, myocardial infarction, venous thromboembolism, acid lipase disease, amyloidosis, Barth Syndrome, biotinidase deficiency, camitine palmitoyl transferase deficiency type II, central pontine myelinolysis, muscular dystrophy, Farber's Disease, glucose-6-phosphate dehydrogenase deficiency, gangliosidoses, trimethylaminuria, Lesch-Nyhan syndrome, lipid storage diseases, metabolic myopathies, methylmalonic aciduria, mitochondrial myopathies, mucopolysaccharidoses, mucolipidoses, mucolipidoses, mucopolysaccharidoses, multiple CoA carboxylase deficiency, nonketotic hyperglycinemia, Pompe disease, propionic acidemia, type I glycogen storage disease, urea cycle disorders, hyperoxaluria, oxalosis, carcinoma, sarcoma, germ cell tumors, blastic tumors, prostate cancer, lung cancer, colorectal cancer, bladder cancer, cutaneous melanoma, breast cancer, endometrial cancer, and ovarian cancer.

In one aspect, provided are methods of treating skin wounds in a subject in need thereof using the activated stem cells or differentiated cells derived therefrom as disclosed herein. In one aspect, provided are methods of treating liver damages in a subject in need thereof using the activated stem cells or differentiated cells derived therefrom as disclosed herein. In one aspect, provided are methods of treating bone damages or conditions (e.g., arthritis, osteoporosis, etc.) in a subject in need thereof using the activated stem cells or differentiated cells derived therefrom as disclosed herein. In one aspect, provided are methods of treating nerve injuries or neuron degenerative diseases in a subject in need thereof using the activated stem cells or differentiated cells derived therefrom as disclosed herein. In one aspect, provided are methods of treating heart tissue damages or heart failure in a subject in need thereof using the activated stem cells or differentiated cells derived therefrom as disclosed herein. In one aspect, provided are methods of treating chronic diseases such as diabetes in a subject in need thereof using the activated stem cells or differentiated cells derived therefrom as disclosed herein.

In one aspect, provided are methods of autologous transfer of the activated or differentiated cells as disclosed herein. In one aspect, provided are methods of allogeneic transfer of the activated or differentiated cells as disclosed herein. In one aspect, provided are methods of syngeneic transfer of the activated or differentiated cells as disclosed herein.

EXAMPLES

Example 1

Isolation of Dormant Tiny Cells from Blood

The following method was used to isolate dormant tiny cells as disclosed herein from peripheral blood of mice. The peripheral blood was collected from FVB-Tg (CAG-luc-eGFP) L2G85Chco/J (L2G) male or female mice harvested at 4-10 weeks of age (The Jackson Laboratory, Sacramento, CA). The luc-eGFP transgene is directed by the CAG promotor (human cytomegalovirus immediate early promoter enhancer with chicken β-actin/rabbit β-globin hybrid promoter) that expresses enhanced green fluorescent protein (eGFP). To collect peripheral blood, the mice were anesthetized in a chamber supplied with 3% isoflurane (Butler Schein Animal Health, Encinitas, CA), and then injected with 4 U of heparin diluted in 100 µl of saline through retro-orbital veins. After 5 minutes, the blood was collected through the retro-orbital sinus from each mouse into a 1.5-ml micro-centrifuge tube containing 1 U of heparin in 100 µl of saline. The blood collected from each mouse was about 1 ml to 1.5 ml routinely.

To lyse the red blood cells, 1 ml of the collected blood was mixed with 9 ml of lysis buffer (e.g., 8.3 g/L of $NH_4Cl$, 1 g/L of $KHCO_3$, and 3.7 g/L of EDTA). The suspension was then centrifuged at 3,000×g for 10 minutes at 4° C. The pellet was washed and resuspended in 3 ml of PBS. To deplete platelets, the cell suspension was transferred to a tube containing a 1:4.4 dilution of Optiprep Density Gradient Medium (Sigma-Aldrich, St. Louis, MO, USA) with PBS to a density of 1.063. The nucleated cell suspension was collected and centrifuged at 350 g for 15 minutes at 4° C. The supernatant was removed and the pellet was resuspended in 10 ml of PBS or culture medium (e.g., α-MEM with 20% FBS) for further analysis.

Figure 2:
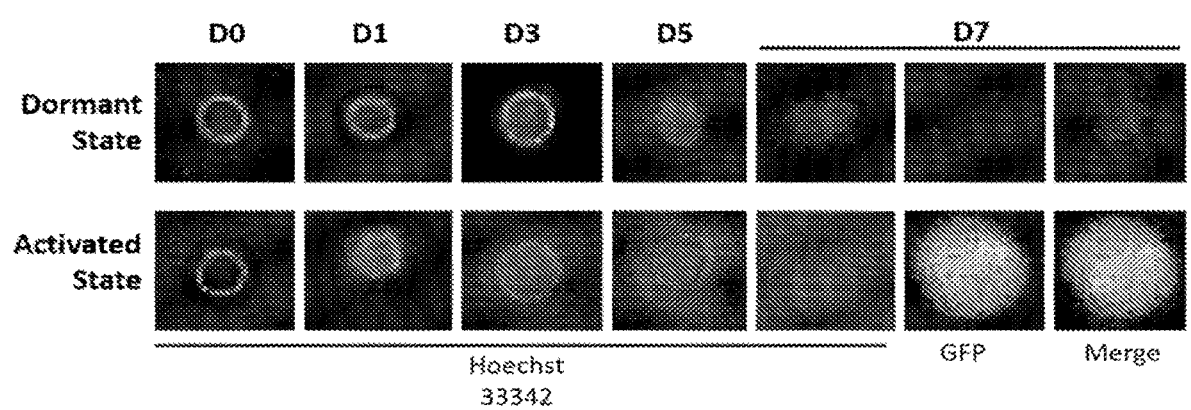
FIG. 2 is an illustration showing nucleus staining of dormant tiny cells and activated stem cells derived therefrom for up to 7 days in vitro, as well as GFP expression in the cells at day 7.
Figure 3A:
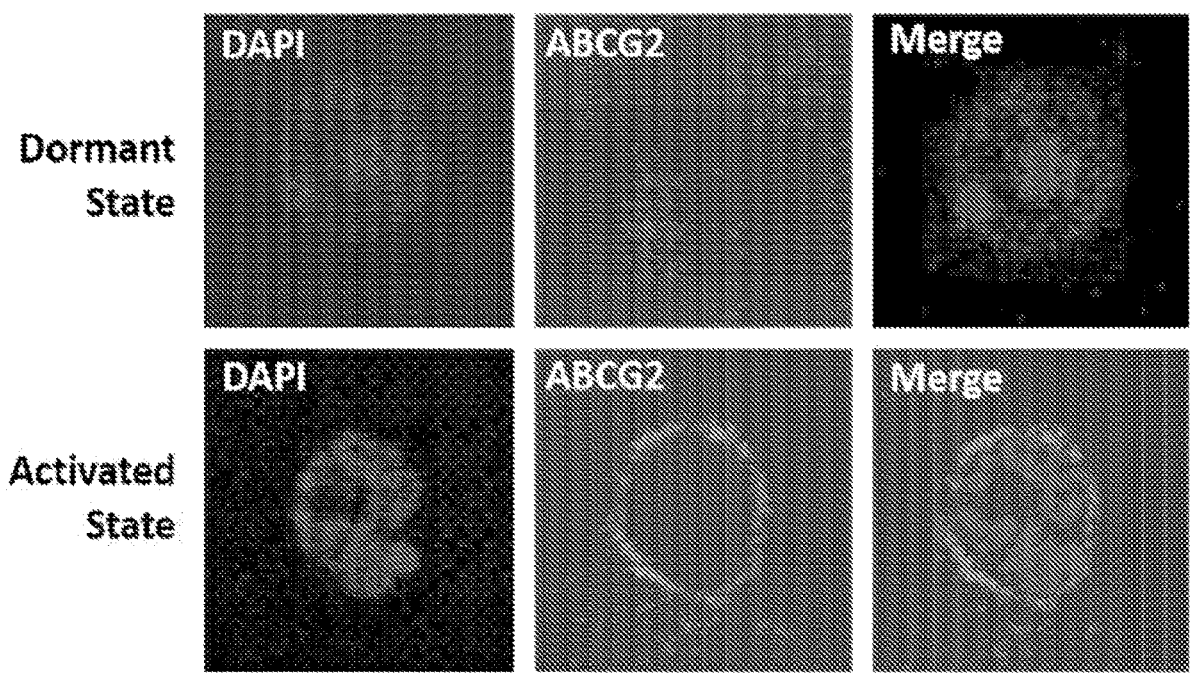
FIG. 3A is an illustration showing ABCG2 expression in the dormant tiny cells and the activated stem cells derived therefrom.
Figure 3B:
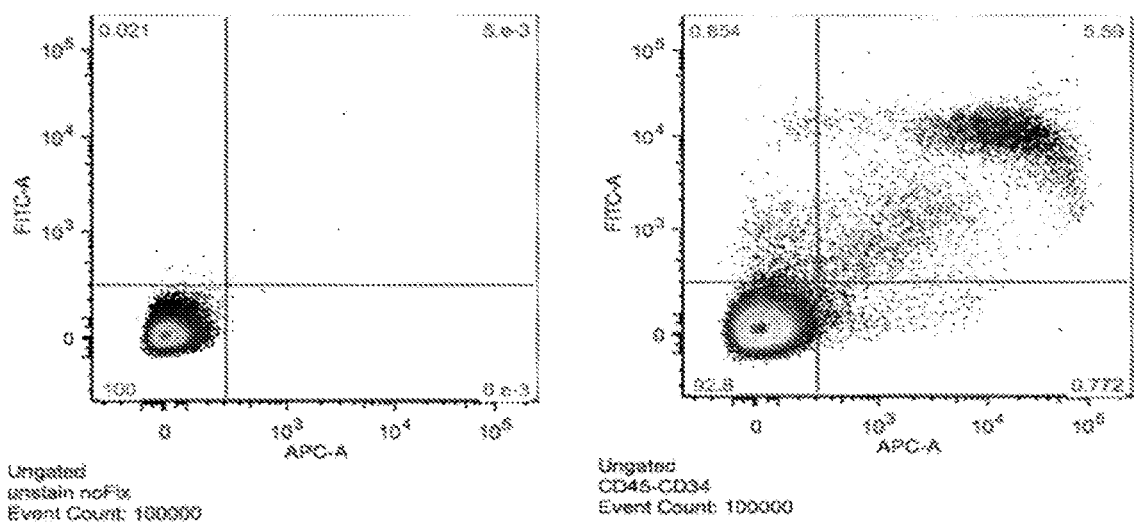
FIG. 3B is an illustration showing a population of cells express CD34 and CD45, which are isolated and characterized as the dormant tiny cells.

Cell counting was performed and the number of cells in the resuspended pellet was between 800,000-1,000,000/ml. The percentage of broken stem cells was below 25%. The isolated stem cells were observed under electron microscope (EM). The diameter of the isolated dormant tiny cells was below 5 µm. For example, the diameter of an isolated dormant tiny cell was measured at about 2.5 µm (FIG. 1). The nucleic acid of the isolated stem cells were stained using Hoechst 33342. The results showed that the isolated stem cells had a very high nucleus-cytoplasm ratio, e.g., at about 9:1 (FIG. 2). When cultured in the regular medium (e.g., α-MEM with 20% FBS) up to 5-10 days, the isolated dormant tiny cells did not grow and the Hoechst 33342 nucleic acid staining did not diffuse outside of the cell membrane (FIG. 2). Immunofluorescence (IF) and fluorescence-activated cell sorting (FACS) analysis were used to test cell markers expressed by the isolated dormant tiny cells, which were characterized as $CD34^+/CD45^+$ and $ABCG2^-$ (FIGS. 3A and 3B).

Figure 4:
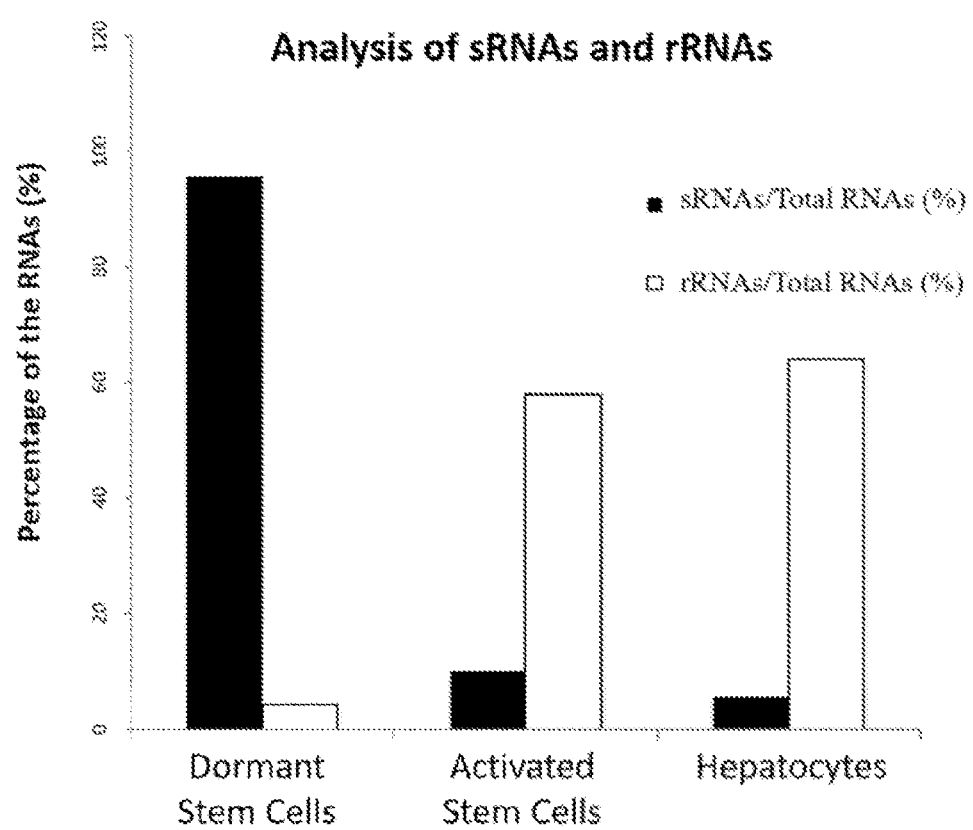
FIG. 4 is an illustration showing ratios of sRNA to rRNA in the dormant tiny cells and the activated stem cells derived therefrom, compared to hepatocyte cell line as control.

Total RNA was extracted from the isolated dormant tiny cells and control cells (wild-type hepatocytes) using the Trizol reagent method and then treated with RNase-free DNase to remove contaminated DNA. The total RNA was analyzed using a microfluidics-based platform of Agilent 2100 Bioanalyzer (Agilent Genomics) to detect and analyze the levels of sRNA and rRNA. The results showed that in the isolated population of dormant tiny cells, the ratio of sRNA to rRNA was about 22:1, compared to a ratio of about 1:10 in hepatocyte cell line (e.g., AML12) (FIG. 4). The levels of COX IV (mitochondrial inner membrane protein), Calnexin (ER-resident molecular chaperone), and RPS3 (ribosome marker) were also tested. The results showed that the isolated dormant tiny cells expressed very low levels of COX IV and Calnexin, and had minimum level of RPS3. The results indicated that the isolated stem cells were in a dormant state.

The dormant tiny cells were also studied for expression of various stem cell markers via FACS. The results demonstrated that the dormant tiny cells expressed, besides CD34 and CD45, some or all of the markers CD44, CD150, Sca1, c-kit, Thy1.1(CD90.1), Oct 4, SSEA1, Nanog, Vasa, CD133, and CD105. The dormant tiny cells were further characterized to be negative in Lin. In addition, the dormant tiny cells did not express some or all of CD41, CD184, and E-cadherin.

Example 2

Activation of Dormant Tiny Cells and Development In Vitro

The following method was used to activate and culture the dormant tiny cells obtained from blood as described in EXAMPLE 1 above.

To activate and culture the dormant tiny cells in vitro, an activation/development system was prepared using materials that included one or more of primary hepatocytes, human hepatoblastoma (HepG2) cells, hepatocyte cell line (e.g., AML12, HepaRG, etc.), and mouse embryo fibroblast (MEF) cell line. Other reagents and factors may be added to the activation/development system. The activation/development system may be a co-culture system using Transwells, or may use conditioned medium, as described below.

Activation In Vitro

For a coculture system, cells or a cell mixture were prepared that include one or more of the above-mentioned cells/cell lines. For example, a cell mixture included, based on total number of cells, about 65-90% of the above-mentioned hepatocyte cell line and about 35-10% of primary hepatocytes. The cell mixture was treated with Mitomycin C for 2 hours to mitotically inactivate the cells. The cell mixture was then inoculated on 6-well plates in DMEM/F12 with 10% FBS. About sixteen hours after inoculation, the cells adhered to the wells and were approximately 80% confluent. Then the isolated dormant tiny cells were placed into the upper chamber of a Transwell (24-mm insert, Corning, Corning, New York), to be co-cultured with the above-mentioned cell mixture in a coculture medium of α-MEM with 20% FBS. The isolated dormant tiny cells were separated from the inactivated cell mixture by the Transwell membrane (0.4 m pore size). The same culture medium was used and changed every other day for both upper and lower chambers, for about 10 to 20 days.

Alternatively, conditioned medium was prepared that could be used to culture the isolated dormant tiny cells in vitro. For example, the above-mentioned cells or cell mixture were suspended in DMEM medium with 10% FBS and then seeded in a cell culture dish. The medium was collected from the cell culture dish every 2 days, and then new medium was added to the cell culture dish until the cells reached 100% confluence. The medium collected at different time can be mixed together, and can be stored at −20° C. for short term storage or at −80° C. for long term storage. Before use, the conditioned medium was centrifuged at 3000×g to pellet the remaining cells in the medium. The conditioned medium can also be filtered with the 0.22 m filter to remove the remaining cells. Then the conditioned medium was mixed with regular cultural medium (e.g., α-MEM with 20% FBS) in a ratio (v/v) of about 1:3 to about 3:1. The isolated dormant tiny cells were gently resuspended in the above-mentioned medium mixture, and then were seeded in culture dishes or plates. The medium may be changed every other day. The cell culture was observed every day under microscope for cell growth and formation of cell colonies.

The activated stem cells, after being cultured in the above-mentioned activation/development system for 4-12 hours, were studied for expression of various markers. ABCG2, which was a marker for undifferentiated cells and not expressed in the dormant tiny cells, was observed to be expressed in the activated stem cells (FIG. 3A). RNA analysis indicated that the ratio of small RNA to ribosomal RNA in the activated stem cells was about 1:6, significantly lower than that in the dormant tiny cells (FIG. 4). The activated stem cells were cultured in the activation/development system up to 15 days, and the Hoechst 33342 nucleic acid staining of the activated stem cells was observed to gradually diffused outside of the cell membrane (FIG. 2). The size of the activated stem cells also became larger than the dormant tiny cells. The activated stem cells were further shown to express high levels of COX IV, RPS3, and Calnexin, as indicated in Table 3, below. Expression of ABCG2 indicated that the activated stem cells were undifferentiated stem cells. The increased expression of COX IV, a mitochondria marker, indicated that the dormant tiny cells had been waked up. The high expression of RPS3, a ribosome RNA (rRNA) marker, indicated that the cells' metabolism was active. The expression of Calnexin, an ER marker, indicated that the transport system in the activated stem cells was busy. These results indicated that the stem cells, which were previously in a dormant state, were activated in the activation/development system, and the cellular functions and activities resumed.

TABLE 3

| Condition | ABCG2 | COX IV | RPS3 | Calnexin |
|---|---|---|---|---|
| Regular Medium (4 hours (hrs)) | — | Very Low | — | Very Low |
| Activation/Development System (4 hrs) | ++++ | ++++ | ++++ | ++++ |

FACS was used to identify the markers of the activated stem cells as described above. The activated stem cells in the activation/development system were characterized into sub-populations that were CD34+/CD45+, CD34+/CD45−, CD34−/CD45+, and/or CD34−/CD45−.

Enrichment and Characterization of Sub-Populations of Activated Stem Cells

The following method was used to obtain a sub-population enriched in activated stem cells that are CD34+. Two weeks after co-culture of the isolated dormant tiny cells in the coculture system as described above, CD34+ cell fractions were enriched by MACS following the protocol recommended by the manufacturer (Miltenyi Biotec Inc. San Diego, CA). Briefly, trypsinized cells were incubated with an anti-CD34 (rat) antibody for 30 min, followed incubation for 15 min at 4° C. with anti-rat Microbeads. After being washed with PBS, cells were resuspended in 500 µl of separation buffer and applied onto a MACS Column (Miltenyi Biotec). The enriched and expanded cells were analyzed for CD34 positivity as well as other surface markers (e.g., CD45, CD44, CD29, CD38, CD3, Lin, Sca-1, Thy1.1, c-kit) by FACS. The isotype IgG was used as a negative controls. Data were analyzed using FlowJo (Tree Star, Ashland, Oregon). Alternatively, FACS could also be used to sort and isolate sub-populations of cells having specific marker(s). Similar method can be used to obtain enriched sub-populations of cells characterized in other marker(s), for example, a sub-population of CD45+ cells, a sub-population of CD34+/CD45+ cells, a sub-population of CD34+/CD45− cells, a sub-population of CD34−/CD45+ cells, or a sub-population of CD34−/CD45− cells.

Immunofluorescent Staining

Indirect immunofluorescence staining was performed using a standard procedure. Briefly, rehydrated paraffin- or fixed frozen-tissue sections at a 5-µm thickness were blocked with 1% BSA/PBS (30 min), washed three times with PBS. The sections were stained with specific primary antibodies and fluorescent-conjugated secondary antibodies. The samples were mounted with DAPI (4, 6-diamino-2-phenylindole dihydrochloride; Vector Laboratories) containing sealant. Mouse IgG and rabbit IgG antibodies was used as negative controls. The stained sections were viewed with a Leica DMRA microscope.

Cell Colony Isolation and Purification

Figure 5:
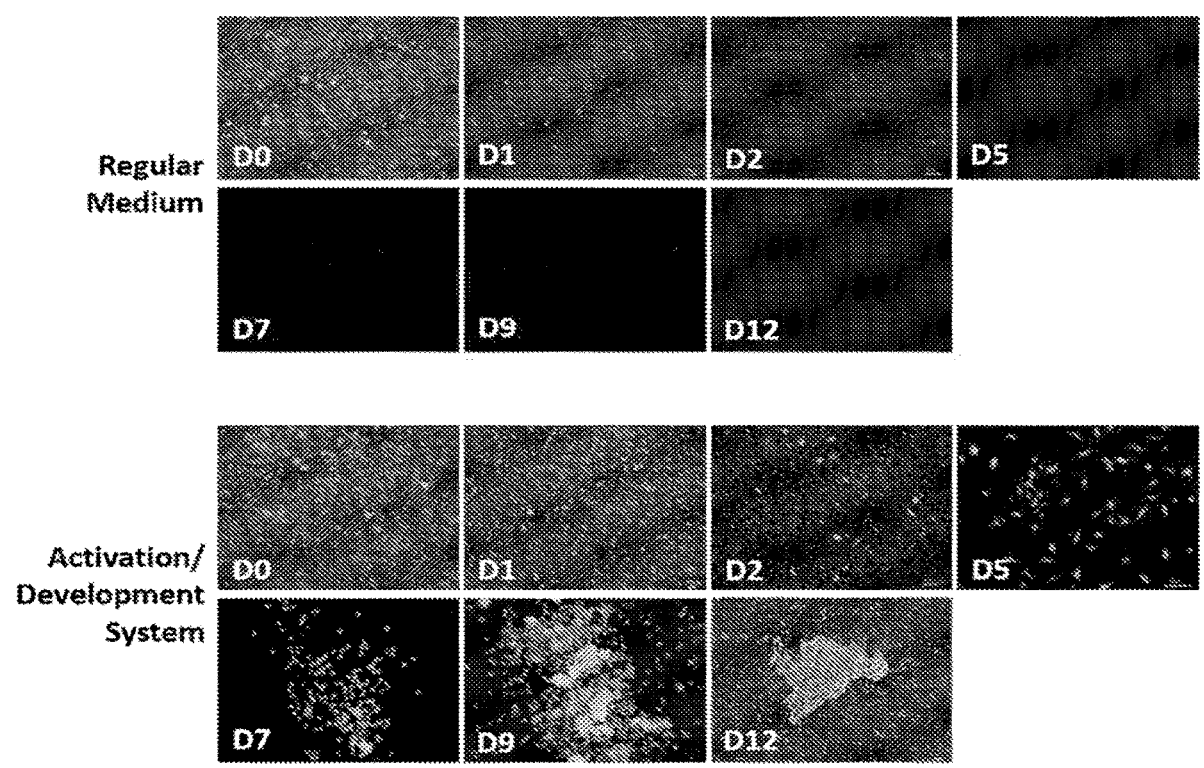
FIG. 5 is an illustration showing growth and expansion of the dormant tiny cells in an activation/development system, and formation of stem cell colonies.
Figure 7:
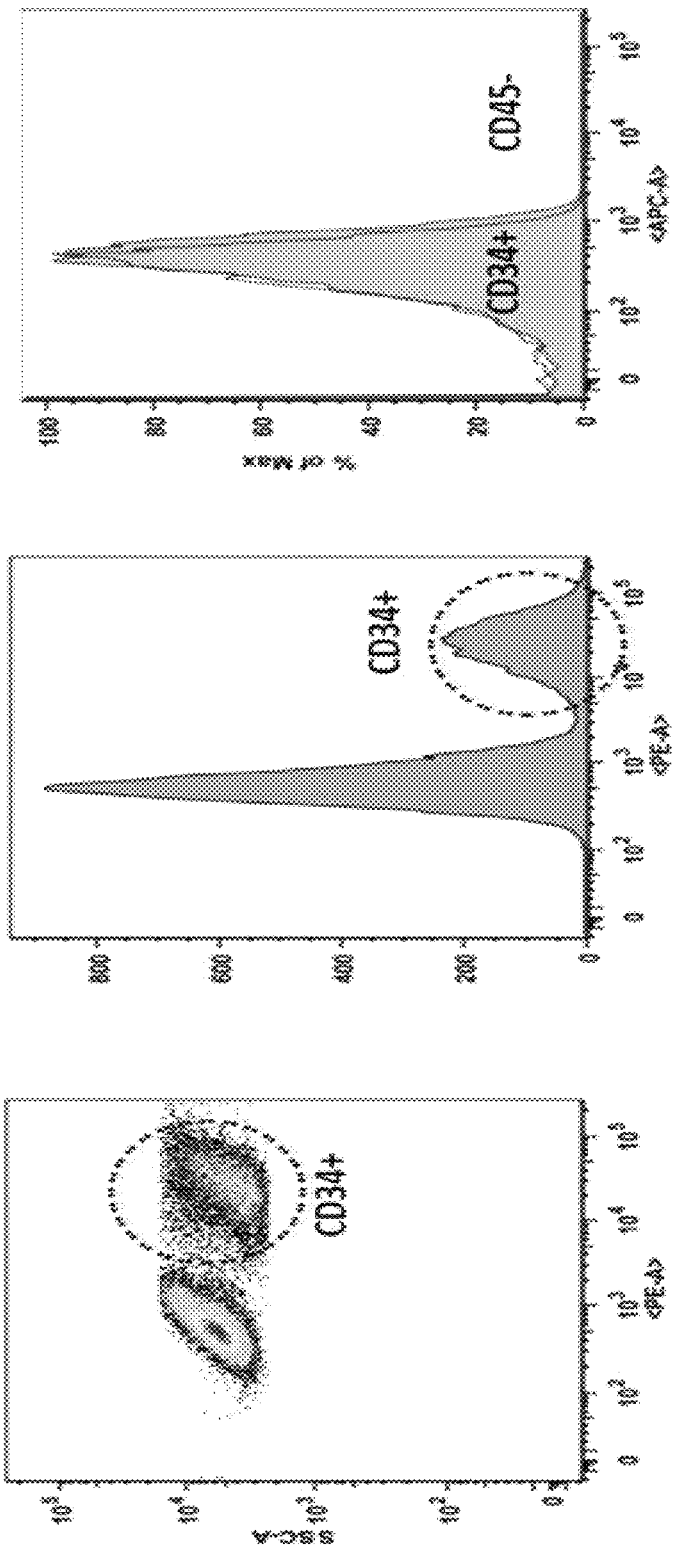
FIG. 7 is an illustration showing the purified population of stem cells express CD34 marker but do not express CD45.

The isolated dormant tiny cells were cultured for 10-20 days in the activation/development system, and one or more cell colonies were observed under microscope (FIG. 5). The cell colonies were then isolated using cloning cylinders or by trypsinizing and detaching the colonies. FACS analysis showed that at least 90% of the stem cells in the isolated colonies were CD34+/CD45− (FIG. 7). A sub-population enriched in CD34+/CD45− cells were purified from the isolated cell colonies by MACS following the protocol recommended by the manufacturer (Miltenyi Biotec Inc. San Diego, CA). For example, the cells of the isolated colonies were incubated with anti-CD45 antibody for 30 min, followed incubation for 15 min at 4° C. with anti-rat Microbeads. After being washed with PBS, the cells were resuspended in 500 µl of separation buffer and applied onto a MACS Column (Miltenyi Biotec Inc. San Diego, CA). The CD45 depleted cell population was collected and was further incubated with anti-CD34 antibody for 30 min, followed incubation for 15 min at 4° C. with anti-rat Microbeads. After being washed with PBS, the cells were resuspended in 500 µl of separation buffer and applied onto the MACS Column. The CD34+ cell population was collected, which was characterized as CD34+/CD45−. Alternatively, the cells in the isolated colonies were labeled with anti-CD34 and anti-CD45 antibodies. Then fluorescence-activated cell sorting (FACS) was performed to sort and collect the CD34+/CD45− cell population.

The purified CD34+/CD45− stem cells, when observed under microscope, had a general spindle or oval shape with high nucleus-cytoplasm ratio (e.g., about 5~8:1) (FIGS. 6, A and B) and a diameter of about 20-30 µm. The purified stem cells express GFP (FIG. 6, A) and were able to expand quickly (e.g., at about 26 hours doubling time) in α-MEM with 20% FBS. The purified stem cells may be cultured in vitro in adherent cell culture and/or suspension cell culture. When the purified stem cells adherent to cell culture dish/plate reached confluency, the cell arrangement resembled epithelial cell culture (FIG. 6, B). A single cell dilution of the activated stem cells was performed. A colony arose from a single cell can be obtained when cultured in the conditioned medium as described above, which had embryoid body-like (EB-like) structure (FIGS. 6, C and D).

The CD34+/CD45− cell population was further studied for stem cell markers using immunofluorescence (IF) staining. The results showed that the purified cell population also expressed one or more early stage markers (e.g., Oct4, Sox2, Nanog, Vasa, SSEA1), hematopoietic markers (e.g., CD34, CD14, CD19, CD117), MSC markers (e.g., CD44, CD73, Thy1.1 (CD90.1), CD105, CD106, Sca1), epithelium markers (e.g., keratin epithelium, CK18, CK19), neural stem cell markers (e.g., Nestin), osteoblast markers (e.g., Osteocalcin), endothelium markers (e.g., CD31), cell migration markers (e.g., CD184), cell integrin markers (e.g., CD29), multi-types stem cell (neuron, HSC, endothelium) markers (e.g., CD133). The purified cell population was further characterized to be negative in one or more of CD3, CD4, CD8a, CD11b, CD13, and CD140a.

Example 3

Induction of Differentiation of Activated Stem Cells

The following method was used to induce the differentiation of the activated stem cells as discussed in EXAMPLE 2. The pluripotent differentiation potential of the purified $CD34^+/CD45^-$ stem cell population from the colonies was studied.

Ectoderm

Figure 8:
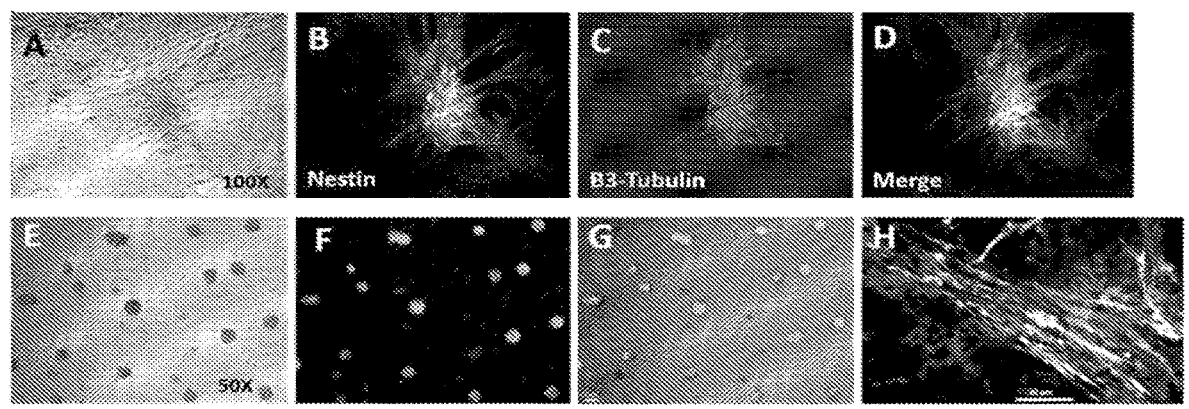
FIG. 8 is an illustration showing that the purified $CD34^+/CD45^-$ cell population can differentiate and express neural cell specific markers.

To study the potential of differentiation into neuronal derivatives (e.g., neurons, oligo-dendrocytes, glial cells), the purified $CD34^+/CD45^-$ stem cells (3,000/well in 24-well plate) were seeded in cell culture dishes/plates and incubated in NeuroCult Basal Medium (Stem Cell Technologies, Vancouver, BC, Canada) supplemented with 10 ng/ml rhEGF, 20 ng/ml FGF-2, and 20 ng/ml NGF (all growth factors from R&D Systems, Minneapolis, MN, USA). Dulbecco's modified Eagle's medium (DMEM) was used in the negative control group. The medium was changed every two days. Neuron mass and neurosphere were formed after about 2 weeks (FIGS. 8, A and E-G). Expression of neural cell specific markers Nestin and 03-Tubulin were observed in the differentiated cells (FIG. 8, B-D). Formation of a bunch of neural cells was also observed, which included neural cells that were positive in Nestin and 03-Tubulin (FIG. 8, H). The results showed that the purified $CD34^+/CD45^-$ stem cells can differentiate into neural cells, which are from the ectoderm layer.

Figure 9:
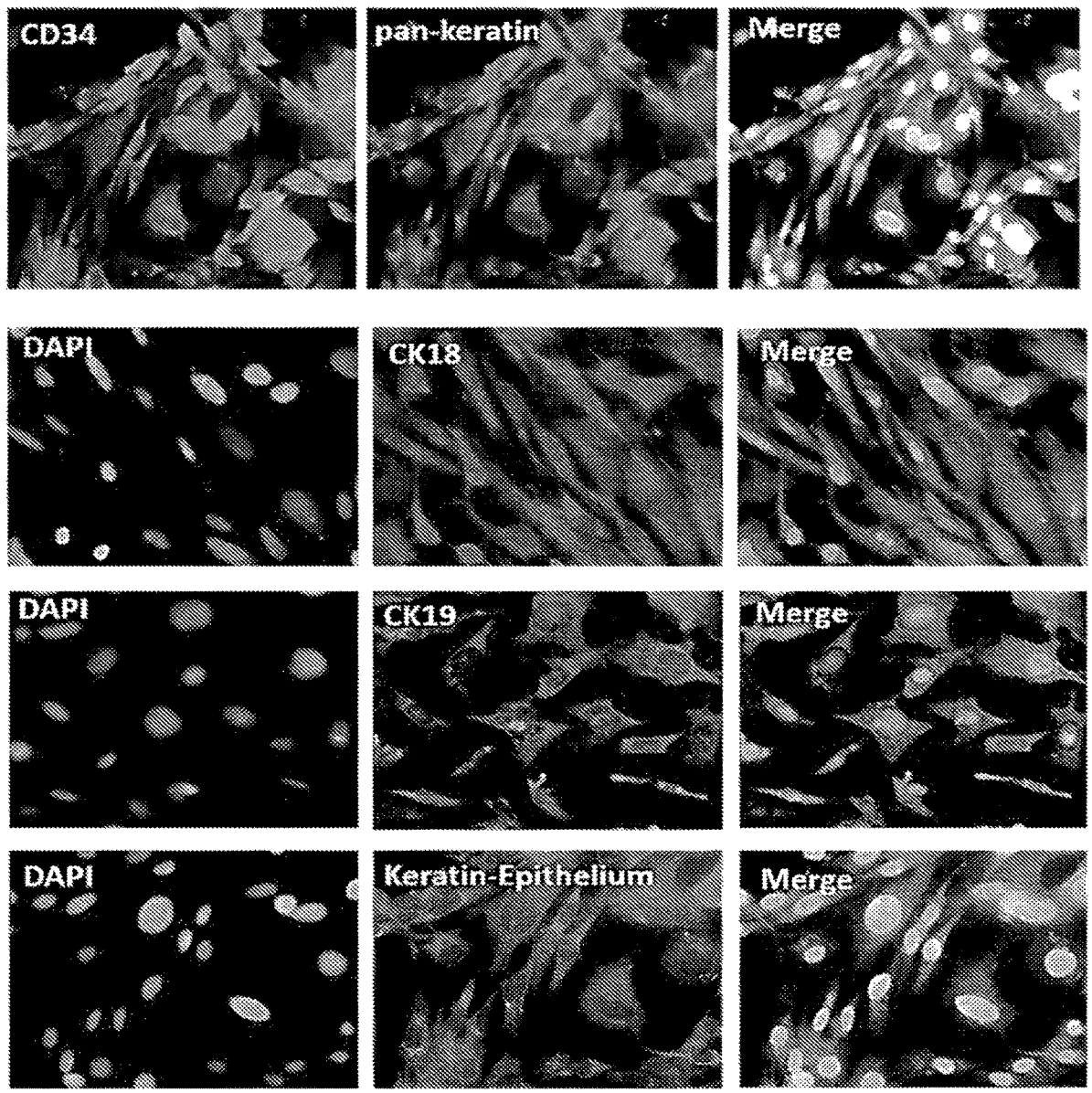
FIG. 9 is an illustration showing that the purified $CD34^+/CD45^-$ cell population can express epidermal markers.

Skin also originates from the ectoderm layer. IF staining was used to test epidermal markers in the activated stem cells. The purified $CD34^+/CD45^-$ stem cells were characterized to express keratin-epithelium markers, CK18, and CK19 (FIG. 9). Expression of pan-keratin (using anti-pan cytokeratin antibody, mouse monoclonal C-11) was also observed in the purified $CD34^+/CD45^-$ stem cells, which overlapped with CD34 staining (FIG. 9). EpCam, the epithelial cell adhesion molecule, was also expressed in the purified $CD34^+/CD45^-$ stem cells, and overlapped with GFP signals. Thus, the results showed that the purified $CD34^+/CD45^-$ stem cells expressed epithelial cell markers and had potential to differentiate into skin cells.

Mesoderm

Figure 10:
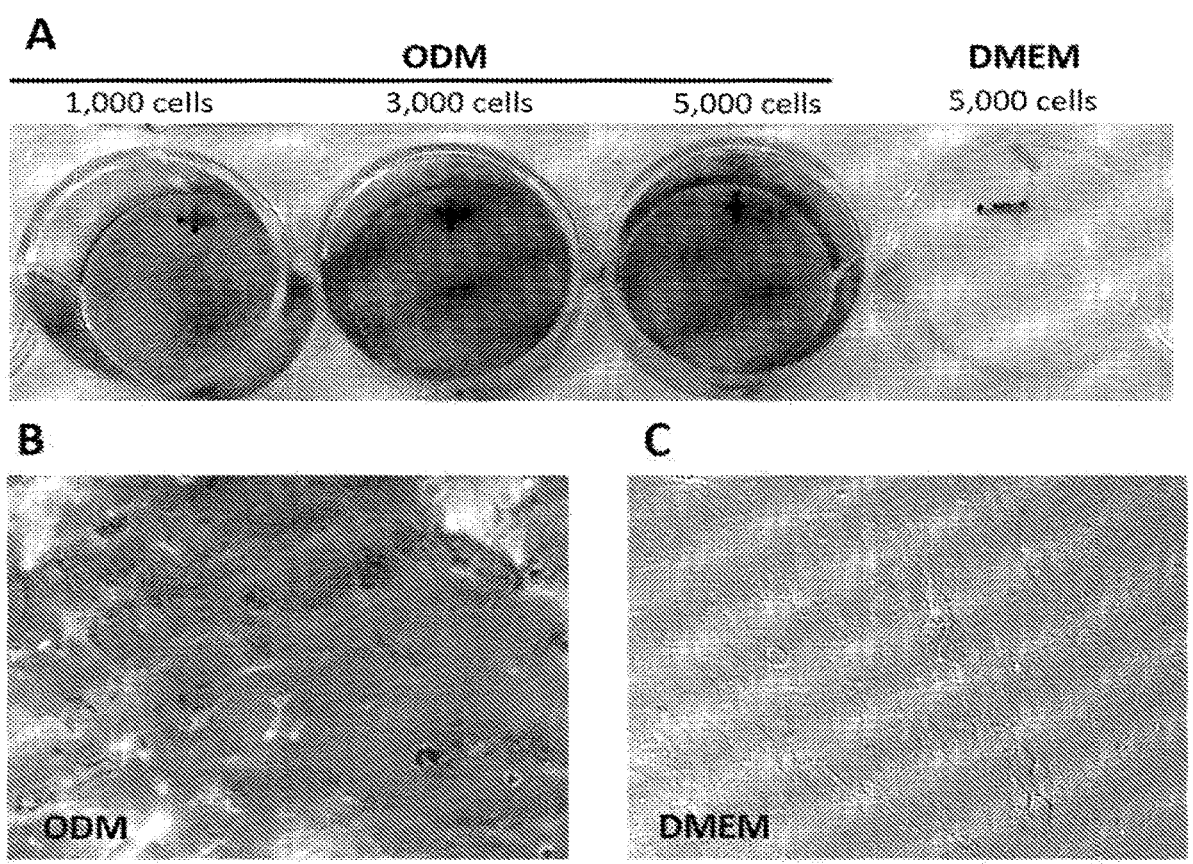
FIG. 10 is an illustration showing that the purified $CD34^+/CD45^-$ cell population can differentiate and express bone tissue specific stain.

To study the potential of differentiation into osteoblasts (mesoderm), the purified $CD34^+/CD45^-$ stem cells (1,000, 3,000, and 5,000 per dish) were seeded in cell culture dishes and incubated with osteoblast differentiation medium (ODM) for two weeks. The ODM may include $\alpha$-MEM containing 10% FBS, 1× penicillin-streptomycin, 0.1 $\mu$M dexamethasone, 10 mM $\beta$-glycerol phosphate, 50 M ascorbic acid. 5,000 of the purified $CD34^+/CD45^-$ stem cells were seeded in $\alpha$-DMEM containing 10% FBS in the negative control group. The medium was changed every two days. After two weeks, the dishes were washed and fixed with 10% formalin, and then stained with Alizarin Red, a bone tissue specific stain. The results showed the formation of ossification center-like structure and the positive staining of Alizarin Red in the dishes of the $CD34^+/CD45^-$ stem cells cultured in the ODM (FIGS. 10, A and B). There was no such ossification structure formed in the control group and the Alizarin Red staining was negative (FIGS. 10, A and B). Thus, the results showed that the purified $CD34^+/CD45^-$ stem cells could differentiate into osteoblasts, cells from the mesoderm layer.

Figure 11:
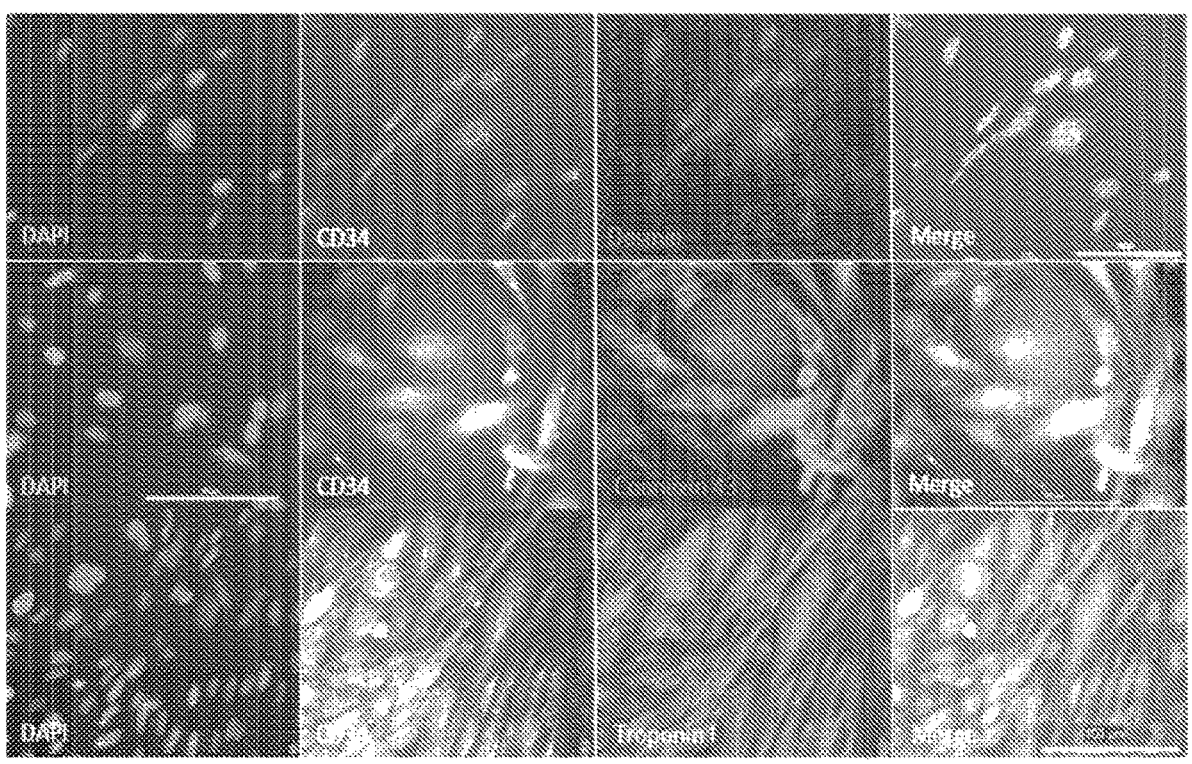
FIG. 11 is an illustration showing that the purified $CD34^+/CD45^-$ cell population can differentiate and express cardiomyocyte specific markers.

To further study the potential of differentiation into cardiomyocytes, another cell type from mesoderm, the purified $CD34^+/CD45^-$ stem cells (about 10,000) were seeded in cell culture dishes and incubated with cardiomyocyte differentiation medium (CDM) for two weeks. $\alpha$-DMEM containing 20% FBS was used in the negative control group. The medium was changed every two days. After two weeks, the cells were stained with CD34, Desmin (a muscle stem cell marker), Connexin 43 (a cardiomyocyte specific marker), and Troponin I (a cardiomyocyte specific marker). All of the markers Desmin, Connexin 43, and Troponin I were positive and overlapped with CD34 (FIG. 11). Thus, the results showed that the purified stem cells could differentiate into cardiomyocytes, cells from the mesoderm layer.

Endoderm

Figure 12:
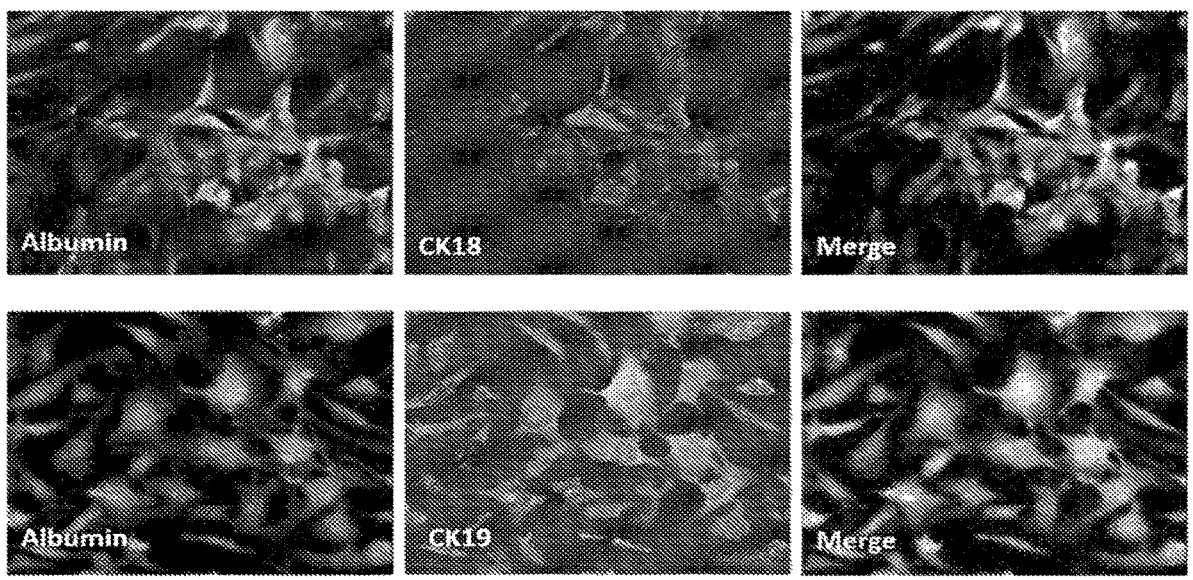
FIG. 12 is an illustration showing that the purified $CD34^+/CD45^-$ cell population can differentiate and express hepatocyte and biliary epithelial specific markers.

To study the potential of differentiation into hepatocytes (endoderm), the purified stem cells were seeded in cell culture dishes and incubated with hepatocyte differentiation medium (HDM) for two weeks. $\alpha$-DMEM containing 20% FBS was used in the negative control group. The medium was changed every two days. After two weeks, the cells were stained with albumin and CK18 (specific hepatocyte markers), and CK19 (a bile duct epithelium marker). All of the markers albumin, CK18, and CK19 were positive (FIG. 12). Further test showed that the albumin staining overlapped with CD34 staining. Thus, the results showed that the purified $CD34^+/CD45^-$ stem cells could differentiate into hepatocyte-like and biliary-like epithelial cells.

Example 4

Treatment of Skin Wounds

The following method was used to treat skin wounds using a population of the activated stem cells as discussed in EXAMPLE 2.

Preparation of the Fibrin Gel Scaffold and the 3-D Construct

Fibrin gels were fabricated by thawing stock solutions of fibrinogen and thrombin and mixing together at final concentration of fibrinogen at 12.5 mg/ml and thrombin at 2.5 U/ml plus $CaCl_2$) (final concentration: 45 mM) in a 1.5 ml tube. 200 $\mu$l of the mixture was gently pipetted into a 24-well plate. The fibrinogen contents were allowed to form fibrin gel scaffolds for 2 hours at 37° C. The activated stem cells (e.g., the enriched $CD34^+$ cell population, or the $CD34^+/CD45^-$ cell population purified from colonies, or other sub-populations) were seeded at $5\times10^5$ on the top of fibrin gel scaffolds per well on the 24-well plate, and were then cultured in $\alpha$-MEM containing 1% heat inactivated fetal calf serum (FCS, BioWest), and 1% penicillin-streptomycin (Gibco) with 2 ml per well over one night. The cell/scaffold 3-D constructs were then ready for transplantation. Before experiments, flow cytometry was also performed to characterize the cultured cells in the cell/scaffold 3-D constructs.

Treatment of Full-Thickness Skin Wounds

After skin preparation, twenty wild-type FVB male mice aged 10 weeks received 6 mm in diameter full-thickness excision wounds on the mid dorsal skin by using an 6-mm biopsy punch (Acuerm Inc., Fort Lauderdale, FL) under isoflurane anesthesia.

To inhibit wound contraction, a donut shaped splints (inner diameter of 10 mm, outer diameter of 14 mm) fabricated from 1.6 mm thick silicone sheet (Press-to-Seal Silicone Sheet JTR-S-2.0, Grace Bio-Labs, Bend, OR) were placed around the wound area and fixed with eight interrupted sutures using 6-0 nylon sutures (6-0 Ethilon Nylon Suture, Ethicon LLC., Cornelia, GA). Then the above-mentioned cell/scaffold 3-D constructs (about 500,000 cells/unit) were transplanted into the wound bed (n=5). The fibrin gel without stem cells (scaffold only) was also transplanted into the wound bed as control (n=5). A trimmed sterile plastic cover slip (Fischer Scientific, Pittsburgh, PA) was placed on top of the splint, and a semi-occlusive dressing (Tegaderm Film 9506 W, 3 M Health Care, St. Paul, MN) was applied circumferentially around the trunk of the animal.

Skin Wound Healing Analysis

Photographic images of wounds were taken every day after generation of wound using a digital camera (Sony cyber-shot DSC-TX 7, New York, NY, USA) from a fixed distance. To have a gross evaluation of the wound area, the wound area was analyzed by calculating the percentage of the current wound with respect to the original wound area. The wound was considered to be completely closed when the wound area was grossly equal to zero.

The mice were euthanized by $CO_2$ at day 15 (D15) and D23 post treatment. The skin wound area and the adjacent tissues (about 2.5 cm) were harvested and fixed in 10% (v/v) buffered formaldehyde for more than 16 hours at 4° C. or passed snap-frozen in liquid nitrogen then process to paraffin embedding or frozen section. Specimens were sliced into 5 μm-thick sections and were stained with hematoxylin and eosin (H&E) to examine local cell degeneration and inflammation. Masson's trichrome collagen staining was performed to assess tissue fibrosis in wound regions. The histological parameters considered were wound closure rate, re-epithelialization, dermal regeneration, fibrous deposition, and inflammation. Regeneration of skin appendages was assessed by counting the number of hair follicles or sebaceous glands in the wound bed. Some paraffin skin sections (5 μm) were further processed for immunohistochemistry (IHC) or immunofluorescence (IF).

Diabetic Skin Wound Model

Diabetic mice (FVB(Cg)-Tg(Ins2-CALM1) 26Ove Tg(Cryaa-TAg)1Ove/PneJ, Jackson Labs) were used to study the wound healing effect of the above-mentioned cell/scaffold 3-D constructs. After skin preparation, six diabetic mice aged 12 months received 1.5 cm×1.5 cm full-thickness skin wounds on the dorsal skin using surgical scissors under isoflurane anesthesia. Then the above-mentioned cell/scaffold 3-D constructs (about 500,000 cells/unit) was transplanted into the wound bed. The fibrin gel without stem cells (scaffold only) was also transplanted into the wound bed as control. Photographic images of wounds were taken every day, for 50 days, after generation of wound using a digital camera (Sony cyber-shot DSC-TX 7, New York, NY, USA) from a fixed distance. To have a gross evaluation of the wound area, the wound area was analyzed by calculating the percentage of the current wound with respect to the original wound area. The wound was considered to be completely closed when the wound area was grossly equal to zero.

The mice were euthanized by $CO_2$ at day 55 (D55) post treatment. The skin wound area and the adjacent tissues (about 2.5 cm) were harvested and fixed in 10% (v/v) buffered formaldehyde for more than 16 hours at 4° C. or passed snap-frozen in liquid nitrogen then process to paraffin embedding or frozen section. Specimens were sliced into 5 μm-thick sections and were stained with hematoxylin and eosin (H&E) to examine local cell degeneration and inflammation. Masson's trichrome staining was performed to assess tissue fibrosis in wound regions. The histological parameters considered were wound closure rate, re-epithelialization, dermal regeneration, fibrous deposition, and inflammation. The results also showed that the regenerated epidermis layer was smooth, and the distribution of collagen was similar to that of the normal skin. The structure and distribution of subcutaneous tissue (e.g., adipose tissue) was clear and similar to that of the normal skin. Muscle tissue neogenesis was also observed.

Statistical Analysis

The images were analyzed to calculate percentage of wound closure rate, percentage of scar area by using image analysis software, a Java-based image processing program (ImageJ, National Institutes of Health, Bethesda, MD, USA). Collagen deposit analysis was based on red color region (cellular structure area) divided by blue color region (collagen deposit) by the method to split color channels with the measure setting in ImageJ. Statistical analysis was performed using a paired, two-tailed, Student's t test to compare 2 groups. A value of $p<0.05$ was considered statistically significant.

Results

To determine the therapeutic potential of the activated stem cells in wound healing, a three-dimensional (3-D) construct was fabricated, which comprises the activated stem cells on a semi-solid fibrin gel scaffold. The construct was applied into a full thickness excisional skin wound created on FVB mice possessing the same strain background to the donor cells from L2G mouse. $GFP^+$ stem cells seeded on the premade fibrin gel for 24 hours before transplantation showed that the cells were growing robustly and to be confluent on the fibrin gel.

Figure 13:
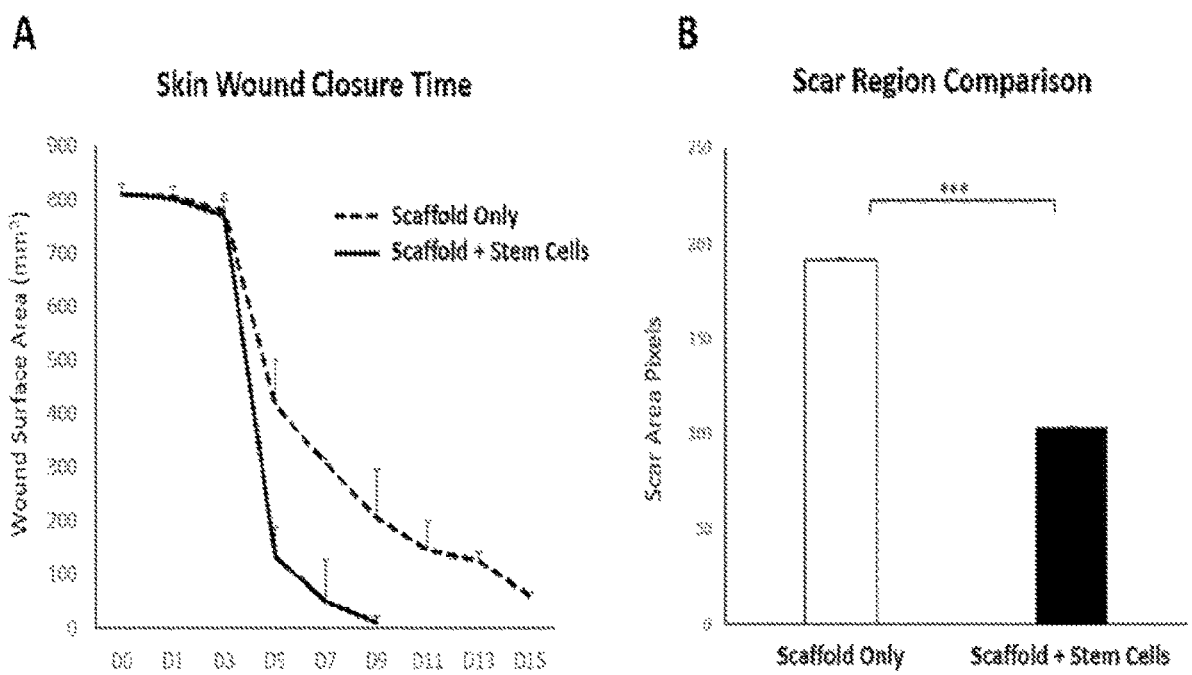
FIG. 13 is an illustration showing faster healing rate of skin wounds in wild-type mice when treated with the purified $CD34^+/CD45^-$ cell population.

The treated group (with the cell/scaffold 3-D constructs) exhibited significantly reduced closure time, scar area, and fibrous tissue deposit (FIG. 13). Morphological image analysis revealed that the treatment with the 3-D construct significantly improved the wound closure as early as day 3 post wounding and became more evident on day 6 post-wounding (FIG. 13, A). Cumulative image analysis revealed a statistically significant improvement in wound healing on days 3, 5, 7 and 9 after treatment compared to the control group. All wound treated with the 3-D construct had closed on day 10 while the wounds in the control group still had opening till day 15 (FIG. 13, A).

Figure 14:
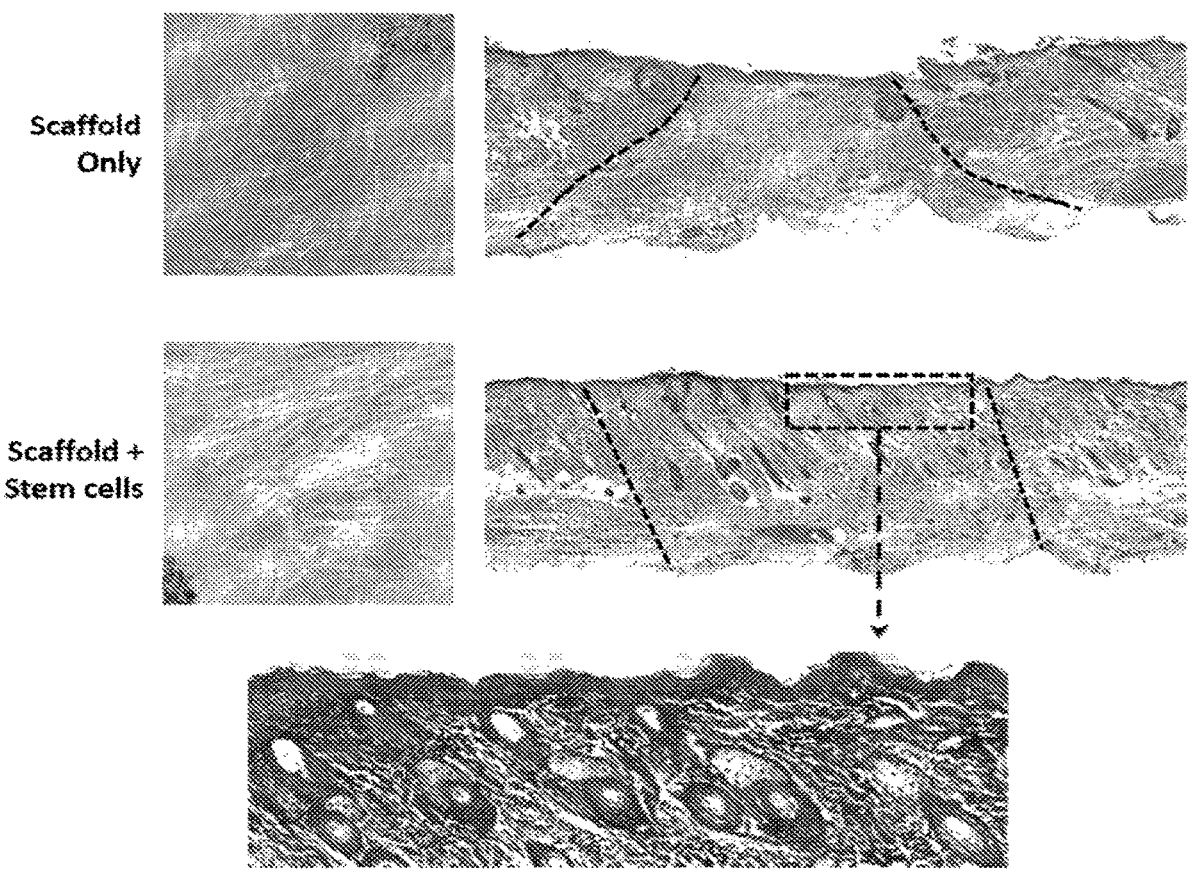
FIG. 14 is an illustration showing growth of new functional skin in the treated mice compared with the scar tissue in the control mice.

Histological evaluation revealed that enhanced re-epithelialization had occurred in the wounds of animals in the treatment group compared to the control group at last day of sacrifice (day 23). At day 6, the wound surface area or scar region was significantly smaller compared to the control group (FIG. 13, B). Higher cell activities were also observed in the wounds in the treatment group, suggesting an enhanced cellular regeneration in these regenerative area. The skin of all treated animals showed nearly normal histological structure of the epidermis and dermis (FIG. 14). The dotted lines outlined the wound area. The 3-D construct stuck on the wound surface. Trichrome staining showed that underneath the 3-D construct, there were many neogenic appendages, with sebaceous gland and hair follicle structures growing into the wound bed and presenting in the wound area of the treated mice (FIG. 14).

Figure 15:
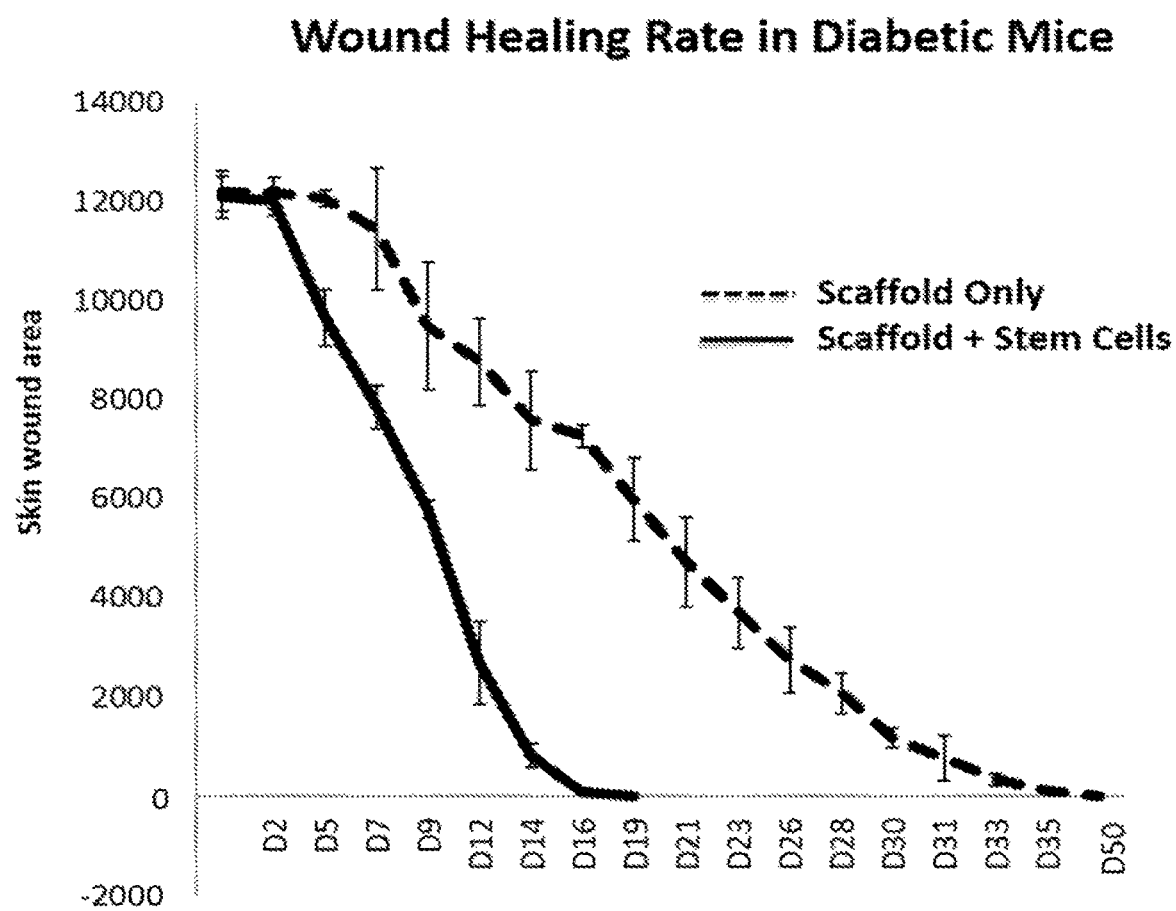
FIG. 15 is an illustration showing faster healing rate of skin wound in diabetic mice when treated with the purified $CD34^+/CD45^-$ cell population.
Figure 16:
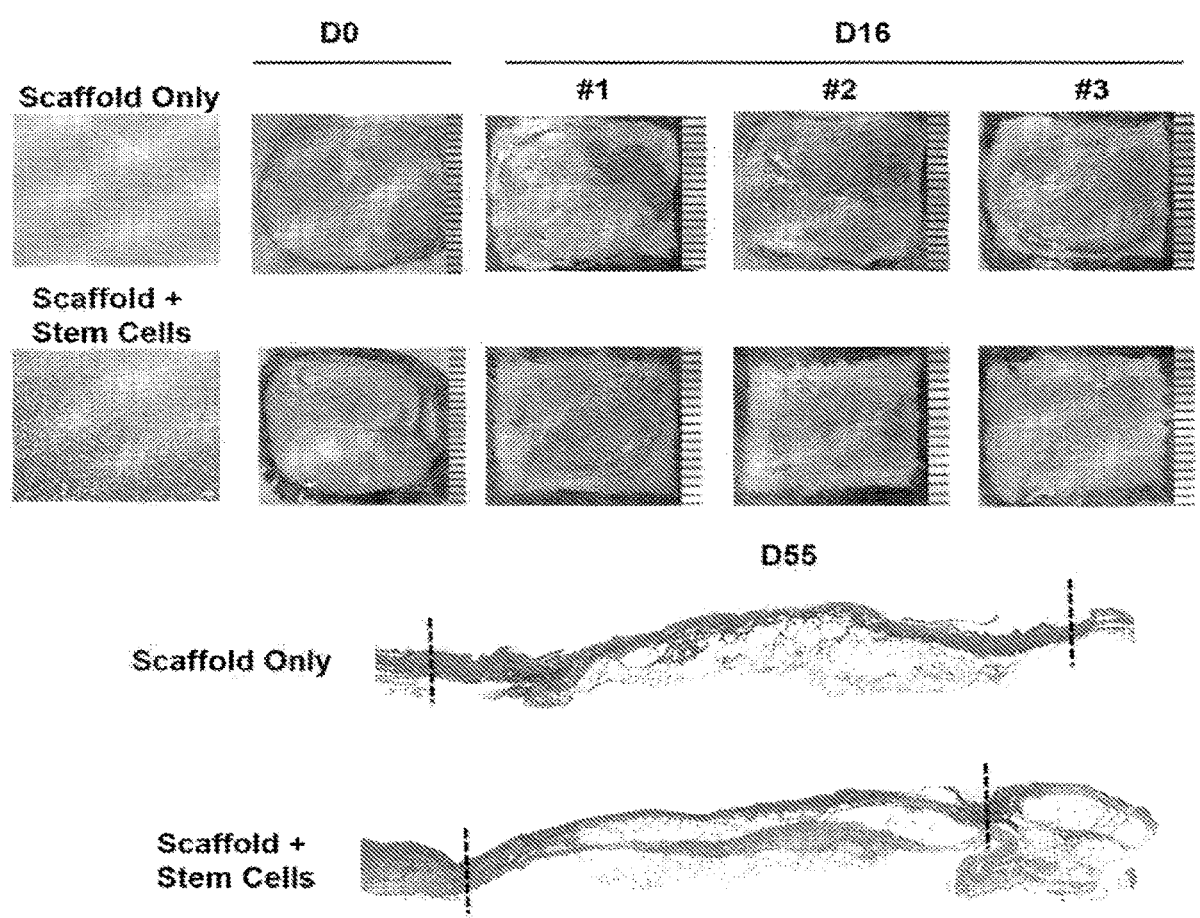
FIG. 16 is an illustration showing growth of new skin after 16 days of treatment in diabetic mice compared with barely closed wound in the control mice.

In the diabetic skin wound model, the results showed that skin wounds in the diabetic mice treated with the cell/scaffold 3-D constructs fully closed at D16-D19 (FIG. 15). The skin wounds in the control group (scaffold only) did not close until D50. Histological evaluation revealed that enhanced re-epithelialization had occurred in the wounds of the mice in the treatment group compared to the control group at last day of sacrifice (day 55) (FIG. 16). The skin of the treated mice showed close to normal histological structure of the skin, with epidermis layer, the subcutaneous tissues, and muscle tissue. In comparison, the wounds in the control group were only closed by a keratinized epidermal layer without subcutaneous tissues and muscle tissue (FIG. 16).

Example 5

Artificial Bone Model

Figure 17:
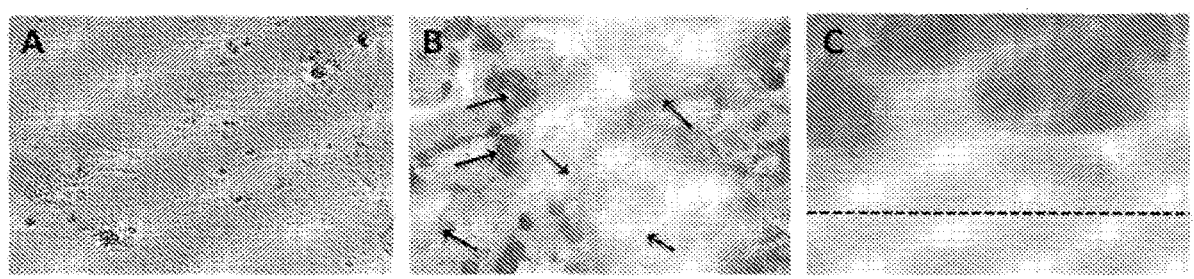
FIG. 17 is an illustration showing growth of bone tissue derived from the purified $CD34^+/CD45^-$ cell population.

The following method was used to develop artificial bone tissue in vitro using the purified stem cells. The purified pluripotent stem cells were seed in a bone matrix and the osteoblast differentiation medium (ODM) was added and cultured for two weeks. At the end of two weeks, mineral deposits was observed (FIG. 17, A). At the third week, some differentiated osteoblasts had connected together to form ossification center-like structure (FIG. 17, B, indicated by arrows). After four weeks, bone tissue had grown, extending from and beyond primary bone matrix (FIG. 17, C, above dotted line). The results showed that the purified stem cells could grow into bone tissue and form artificial bone on the matrix.

Example 6

Treatment of Liver Injury

The following method was used to treat liver injury using the purified $CD34^+/CD45^-$ cell population, as described in EXAMPLE 3.

To establish the liver injury model, one-time peritoneal injections (1.2 ml/kg) of $CCl_4$ diluted 1:1 in olive oil were performed on 20 adult recipient wild-type FVB mice at 8 weeks of age. One day after $CCl_4$ administration, the experimental mice were randomly chosen to accept a one-time intravenous injection with $2.5 \times 10^5$ purified $CD34^+/CD45^-$ cells suspended in 150 µl of saline through the retro-orbital sinus (n=10). The control mice were treated with 150 µl of saline by the same route (n=10). All the mice were sacrificed on day 7 after the transplantation of the purified $CD34^+/CD45^-$ cell. The mouse internal organs were harvested and fixed in 10% buffered formalin. Liver tissue samples were separated for snap freezing and paraffin embedding.

Figure 18:
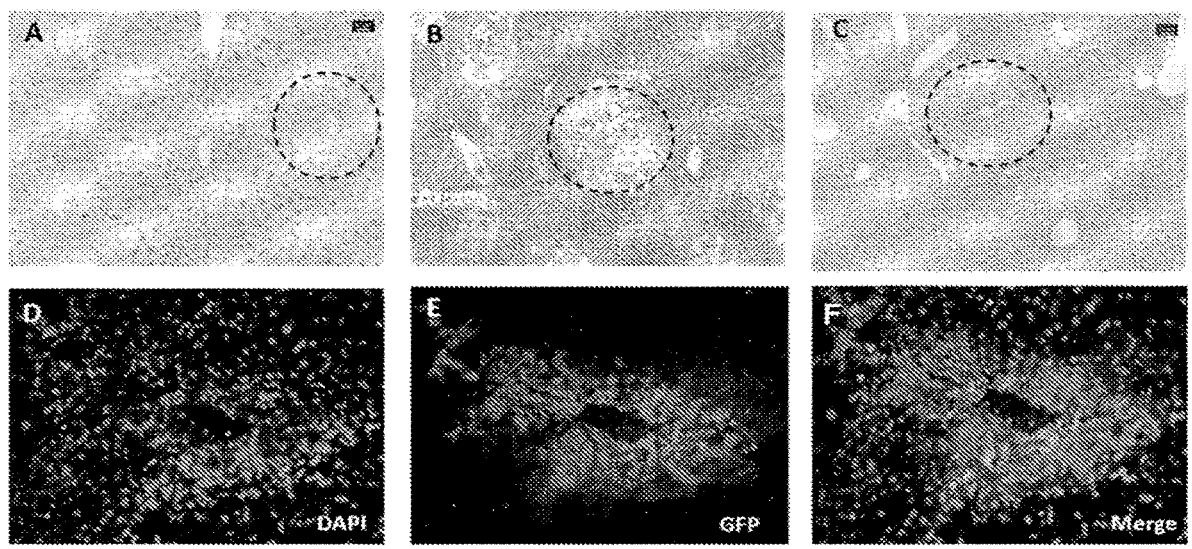
FIG. 18 is an illustration showing repair of liver injury caused by $CCl_4$ after transplantation of the purified $CD34^+/CD45^-$ cell population.

The results showed that hepatocytes in the centrilobular region demonstrated vacuolar, hydropic, and fatty degeneration accompanied by pyknosis, karyorrhexis, and karyolysis in the control mouse livers on day 7 compared with normal livers (FIGS. 18, A and B). In contrast, the mice treated with the purified $CD34^+/CD45^-$ cells demonstrated complete regeneration with nearly normal structure in the central vein area (FIG. 18, C). These results suggested that treatment using the purified $CD34^+/CD45^-$ cells markedly attenuates $CCl_4$ damage and greatly promotes liver regeneration. The inflammatory cells did not infiltrate the regenerated liver area and surrounding tissues after the treatment using the purified $CD34^+/CD45^-$ cells, suggesting little rejection or immune response occurs.

Fluorescent microscopy demonstrated considerable numbers of $GFP^+$ cells in the central vein region, which is the target of $CCl_4$ injury (FIGS. 18, D, E, and F). Transplanted $GFP^+$ cells expressed albumin and the proliferation marker Ki-67. These results suggested that the transplanted purified $CD34^+/CD45^-$ cells are accepted by the host liver and are not transient, but actively proliferate and repopulate the damaged region both structurally and functionally. PCR analysis of the liver tissue showed the long-term presence of the GFP gene in the transplanted liver for at least 3 months. No gross or histologic evidence of hepatic tumor formation was found in the treated livers at all time points.

Example 7

Alternative Methods of Culturing Stem Cells and Treatment of Liver Injury

An alternative method was used to activate and culture the dormant tiny cells isolated from blood, and to use the activated stem cells for treatment of liver injury.

Stem Cell Isolation and Co-Culture

FVB-Tg (CAG-luc-eGFP) L2G85Chco/J (L2G) male mice were harvested at 8 weeks of age (The Jackson Laboratory, Sacramento, CA). The luc-eGFP transgene is directed by the CAG promotor (human cytomegalovirus immediate early promoter enhancer with chicken β-actin/rabbit β-globin hybrid promoter) that expresses enhanced green fluorescent protein (eGFP). The mice were fully anesthetized in a chamber supplied with 3% isoflurane (Butler Schein Animal Health, Encinitas, CA), and then injected with 3 U of heparin diluted in 100 µl of saline. The blood was collected through the retro-orbital sinus from each mouse using a heparinized capillary tube. Red blood cells were depleted by adding lysis buffer (8.3 g/l $NH_4Cl$, 1 g/l $KHCO_3$, 3.7 g/l EDTA at 10:1) to whole blood in a 50-ml tube, followed by high-speed centrifugation at 3,000 g for 10 minutes at 4° C. The pellet was resuspended in 3 ml of phosphate-buffered saline (PBS). To deplete platelets, the cell suspension was transferred to a tube containing a 1:4.4 dilution of Optiprep Density Gradient Medium with PBS to a density of 1.063. The nucleated cell suspension was collected and centrifuged at 350 g for 15 minutes at 4° C. The pellet was resuspended in PBS for further fluorescence-activated cell sorting (FACS) analysis or resuspended in the culture medium (α-MEM with 20% FBS, 13 mg of antibiotic-antimycotic, 20 mg of gentamicin) for in vitro studies. AML12 hepatic cells (ATCC, Manassas, VA) were pre-treated with 30 mg/l mitomycin C for 2 hours. The mitotically inactivated AML12 hepatocytes were then inoculated on six-well plates in DMEM with 10% FBS. Sixteen hours after inoculation, the AML12 cells had adhered to the bottom chamber of culture wells and were approximately 80% confluent. The nucleated cell suspension derived from 0.5 ml of blood was placed into the upper chamber of a Transwell (24-mm insert, 0.4-mm pore size; Corning, Corning, NY). The culture medium was changed every other day.

Magnetic-Activated Cell Sorting (MACS) and FACS Analysis

After 3 weeks of co-culture with mitomycin C treated AML12 cells, the expanded cells were purified with magnetic-activated cell sorting (MACS) to enrich for $CD34^-$ positive cells (Miltenyi Biotec Inc., San Diego, CA). In brief, cultured cells were trypsinized and incubated with an anti-CD34 rat antibody for 30 minutes, washed with PBS, and incubated with anti-rat microbeads at 4° C. for 30 minutes. After being washed with PBS, the cells were resuspended in 500 µl of separation buffer and applied onto a MACS column. Cells from the original, negative, and positive fractions were counted and seeded onto the Transwell membrane as mentioned above. The expanded cells were analyzed for CD34 positivity and different surface markers, including CD45, Sca-1, Thy1.1, c-kit, and CD41 by FACS. Nuclei were stained with 49,6-diamidino-2-phenylindole (DAPI) or Hoechst33342. Data were analyzed using FlowJo (Tree Star, Ashland, OR).

Liver Injury Model and Cell Transplantation

One-time peritoneal injections (1.2 ml/kg) of $CCl_4$ diluted 1:1 in olive oil were performed on 20 adult recipient wild-type FVB mice at 8 weeks of age. One day after $CCl_4$ administration, the experimental mice were randomly chosen to accept a one-time intravenous injection with 2.5×10$^5$ CD34$^+$ cell population, purified from the cocultured stem cells, suspended in 150 µl of saline through the retro-orbital sinus (n=10). The control mice were treated with 150 µl of saline by the same route (n=10). All the mice were sacrificed on day 7 after the transplantation of the purified CD34$^+$ cell population. Blood was collected for laboratory measurements. The mouse internal organs were harvested and fixed in 10% buffered formalin. Liver tissue samples were separated for snap freezing and paraffin embedding. In order to study the mechanism of cell transdifferentiation, mT/mG mice (The Jackson Laboratory, Bar Harbor, ME) were crossed with albumin-Cre transgenic mice (courtesy of Dr. Karl Sylvester, Stanford, CA).

Polymerase Chain Reaction (PCR), Reverse Transcription Polymerase Chain Reaction (RT-PCR), and RNA Analysis DNA was extracted from fresh or frozen liver tissues from the cocultured stem cells, eGFP mice, or transplanted mouse livers using a GENJET Genomic DNA purification kit (ThermoScientific, Vilnius, Lithuania). Total RNA was extracted from MACS-sorted, Hoechst 33342-positive, fresh or cultured stem cells at 3 weeks or control cells (cultured AML12 cells without any treatment) using the Trizol reagent method and then treated with RNase-free DNase to remove contaminated DNA. First-strand cDNA was obtained from 4 µg of total RNA per 100 µl of reaction volume using SuperScript II reverse transcriptase (Life Technologies, Carlsbad, CA). Polymerase chain reaction (PCR) and reverse transcription-PCR were performed in a 20 µl reaction volume with a standard protocol and 1,000 ng of template DNA or cDNA, 10 mM of each primer, and PCR Master Mix (Promega, Madison, WI). 18S rRNA was used as an internal control gene.

Western Blot Analysis

Cocultured cells and AML12 cells were washed three times with PBS and then lysed with RIPA buffer and incubated on ice for 15 minutes. The lysates were centrifuged, and the supernatant was used for Western blot analysis after protein quantification. Cell lysates were transferred to nitrocellulose membrane by electrophoresis. After washing, the protein-loaded membrane was incubated with dry milk to block nonspecific binding. The primary antibody incubation used a rabbit anti-albumin antibody and a j-actin antibody for internal quantity control, at 4° C., overnight. After washing, the membrane was incubated with HRP-conjugated goat anti-rabbit secondary antibody and visualized by enhanced chemiluminescence (GE Healthcare, Little Chalfont, Buckinghamshire, UK). The antibodies used targeted A6, a-fetoprotein (AFP), Albumin, β-actin, CD117 (c-kit), CD34, CD41, CD45, CK8, CK18, CK19, CD29 (integrin β1), Ki-67, proliferating cell nuclear antigen (PCNA), Sca-1, Thy1.1 (CD90.1), and DNA antibody.

Histological and Immunological Staining

Paraffin-embedded tissue specimens were sectioned at 5-µm thickness on glass slides and deparaffinized and rehydrated. Freshly isolated cells, cocultured stem cells and cultured AML12 cells were cytospun onto glass slides or directly tested on the Transwell membrane. The tissue or cell slides and Transwell membranes were stained with hematoxylin and eosin or periodic acid-Schiff (PAS). IHC and IF staining are briefly described as follows: the slides underwent antigen retrieval in 0.01 M citric acid buffer, pH 6.0, in a microwave oven for 5 minutes, followed by incubation with 0.03% H$_2$O$_2$ for 30 minutes to block endogenous peroxidase. The slides and membranes were incubated with 1% horse serum for 30 minutes to block nonspecific binding and then incubated with primary antibodies overnight at 4° C. After washing with PBS, the slides were treated with biotinylated secondary antibodies for IHC or fluorescent dye-conjugated antibodies for IF. Alexa Fluor anti-mouse, anti-rabbit, or anti-rat IgG1 antibodies (1 mg/ml) were used as antibody controls. IF-stained slides were mounted with DAPI and analyzed by confocal microscopy. IHC samples were incubated with ABC complex and then developed with DAB. Double staining was developed with DAB (brown stain) and nickel/DAB (dark blue or gray stain). Diverse control groups, including positive, negative, and blank controls, were set up for each test to ensure the specificity of the antibodies. The images were viewed under a Leica DMRA microscope (Leica, Heerbrugg, Switzerland).

In Situ Imaging of GFP Expression in the Liver

Liver specimens were flushed with cold saline (4° C., 10 ml) and embedded into Cryo-OCT Compound (Sakura Finetek, Tokyo, Japan) directly without fixation to avoid the autofluorescence caused by aldehyde crosslinking. The fluorescence of the GFP signal in liver tissues was measured by fluorescence microscopy.

Statistical Analysis

Statistical analysis was performed using a paired, two-tailed Student's t test to compare two groups. Image analysis was performed with ImageJ (NIH, Bethesda, MD), a Java-based image processing program. Differences were considered significant when $p<0.05$.

Results

Figure 19:
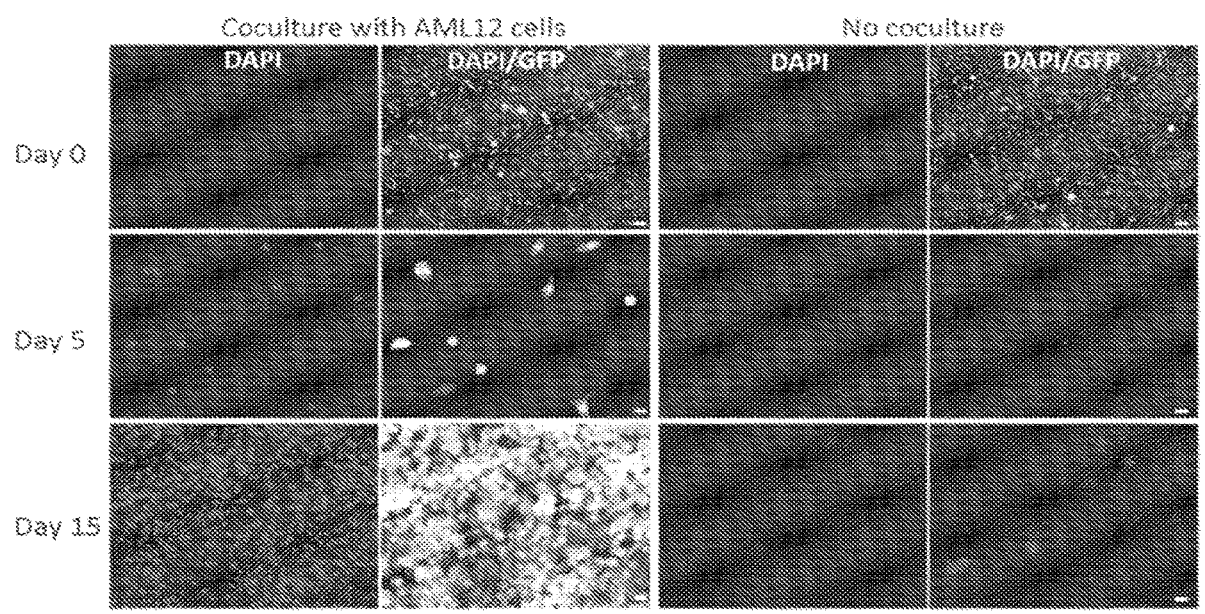
FIG. 19 is an illustration showing an alternative cell culture of the dormant tiny cells isolated from blood in a coculture with the activation/development system.

FACS analysis of freshly isolated nucleated cells from the peripheral blood of L2G or wild-type FVB mice demonstrated a highly heterogeneous cell mixture after red blood cell lysis and platelet depletion. A small fraction of CD34$^-$ positive cells coexpress CD45 (0.04% in two pooled mouse fractions). The nucleated (DAPI$^+$) cell mixture from peripheral blood of L2G (GFP$^+$) mice rapidly expanded during coculture with AML12 hepatocytes (FIG. 19). However, the cell mixture without coculture with AML12 cells did not proliferate and became senescent, with loss of GFP expression by day 5 compared with the cocultured cells (FIG. 19).

After being enriched by MACS, the CD34$^+$ cell dominant group (>90%) expanded more rapidly in the hepatic environment over time. FACS analysis demonstrated that the expanded cells not only expressed CD34 but also expressed CD45, c-kit, Sca-1, and Thy1.1, but not CD41, the molecular marker for blood platelets. Bromodeoxyuridine labeling showed that the CD34$^+$/CD45$^+$ cells doubling time was about 48 hours.

Pronounced morphological changes in expanded cells during AML12 coculture over time were observed. The cocultured cells become elongated, flat, and polygonal, with a decreased nucleus-cytoplasm ratio after 4 weeks of coculture. The cocultured cells expressed a diverse panel of markers for hepatocytes such as a-fetoprotein (AFP), CK8, CK19, and CK18. A6, a specific marker for intrahepatic stem cells, was coexpressed with proliferating cell nuclear antigen (PCNA) and CK19. Coexpression of hepatic epithelial markers CK8 or CK18 and CD34 in the same cocultured cells suggested hepatic epithelial differentiation was occurring. Some cocultured cells demonstrated colocalization of PCNA with A6, suggesting active proliferation of primitive hepatocyte-like cells. CD45 positivity on the cocultured cells growing in situ on the Transwell membrane demonstrated their hematopoietic origin. Hepatic-specific transcription factors and liver metabolic function-related cytochrome P450 (CYPs) genes, such as hepatic nuclear factor 1a (HNF1a), CYP3A16, and CYP1B1, were activated in the cocultured cells compared with AML12 hepatocytes.

Figure 20:
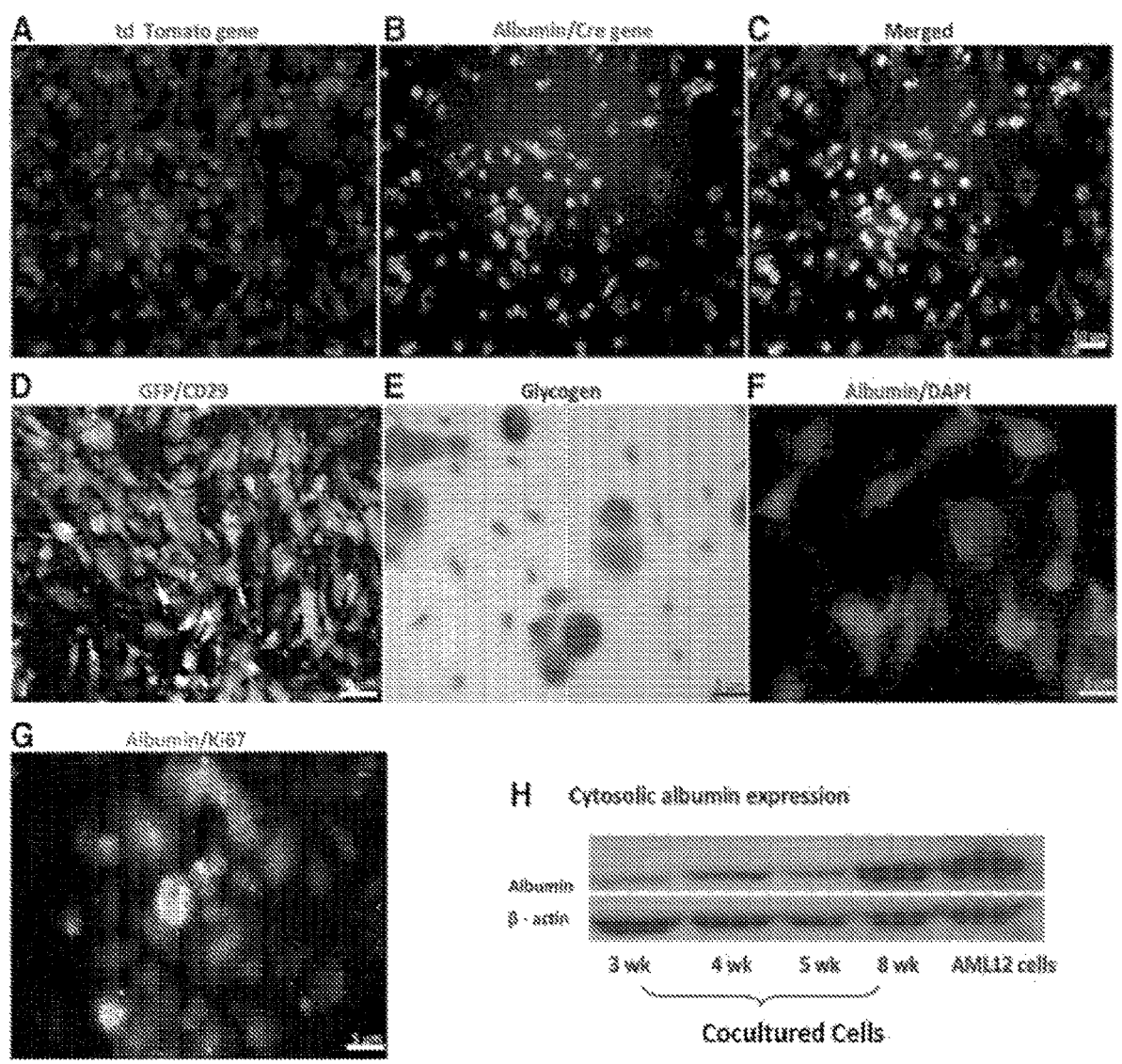
FIG. 20 is an illustration showing expression of hepatocyte specific markers in the stem cells cocultured with the activation/development system.

The transdifferentiation process of the cocultured cells from hematopoietic cells to hepaticepithelialized, albumin-expressing cells under the induction of the hepatic environment was observed. Freshly isolated nucleated cells from mT/mG mice all expressed the Tomato red transgene, as expected (FIG. 20, A). During coculture with AML12 cells, some cells converted to green fluorescence as albumin/Cre transgene was expressed by day 7 (FIGS. 20, B and C). Most cells gradually turned green and expressed GFP over time. CD29, an important regulator of liver functional differentiation, was expressed in the GFP+ cells (FIG. 20, D). Positive PAS staining suggested functional activity of the cells to synthesize and store glycogen (FIG. 20, E), in addition to albumin expression (FIG. 20, F). The growth status of the purified CD34+ cells was explored with Ki-67, a cell proliferation marker. Some cells showed proliferative activity (Ki-67) with albumin expression (FIG. 20, G). Immunoblotting demonstrated increased albumin expression over time in cocultured cells (FIG. 20, H).

Figure 21:
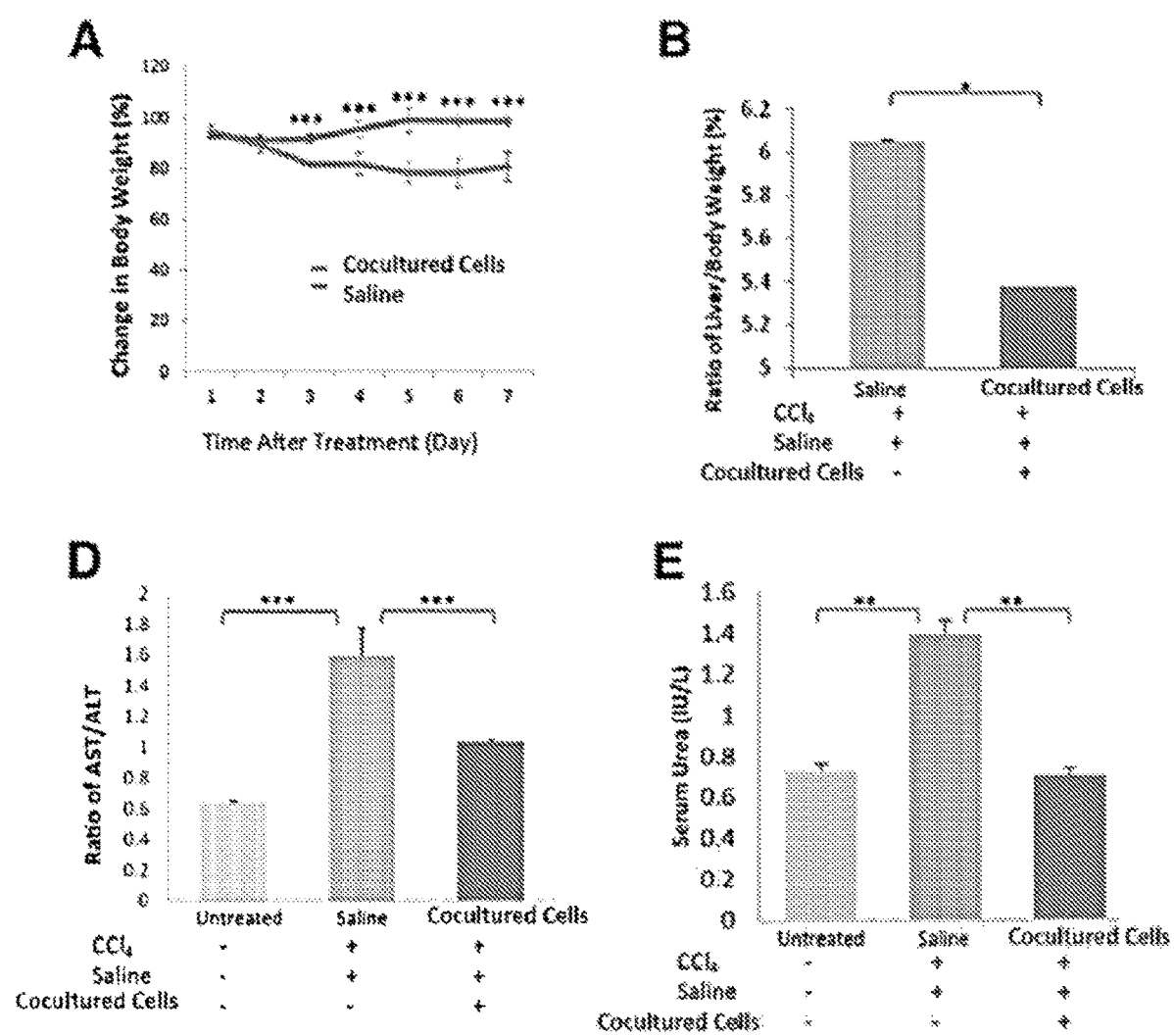
FIG. 21 is an illustration showing treatment of liver injury using stem cells obtained from the cocultured system.
Figure 21:
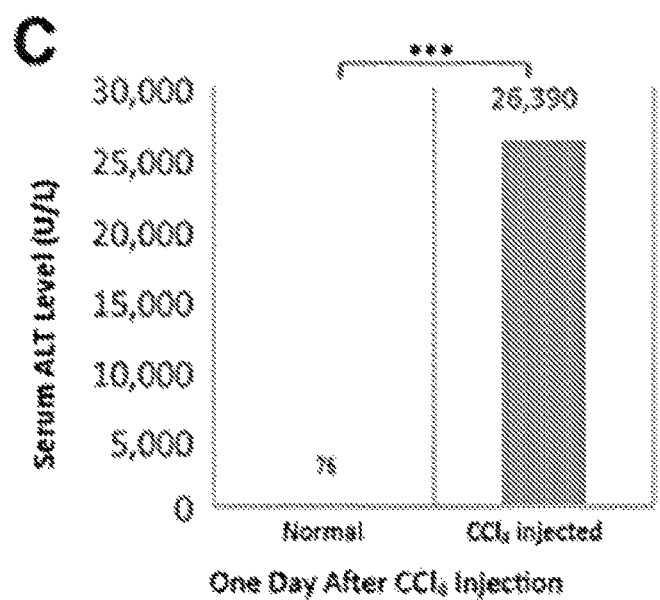
Figure 21:
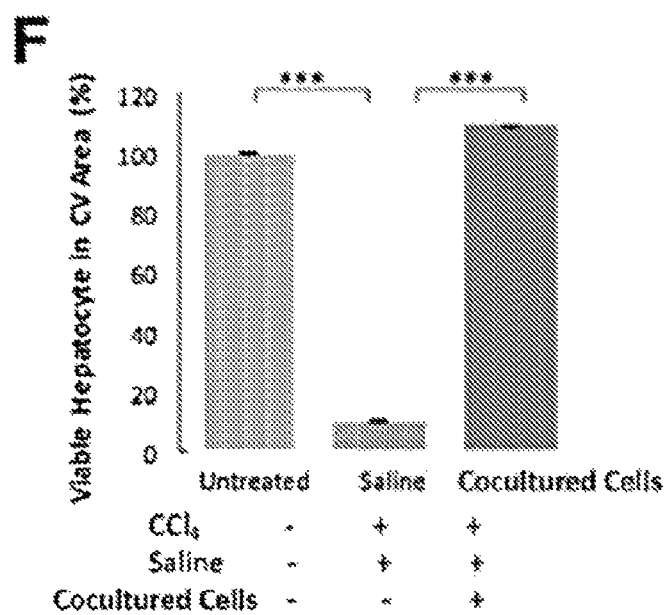

An acute liver injury mouse model was created by high-dose $CCl_4$ injection. Starting at day 1 after injection of $CCl_4$, each mouse lost 1-2 g of body weight (BW) daily. The BW of the mice without treatment using the cocultured cells (saline treated as control) continued to decrease until the mice were sacrificed on day 7, consistent with worsening liver damage (FIG. 21, A). Two mice (20% mortality) died on days 2 and 3 after $CCl_4$ injection. The control mice also had a higher ratio of liver weight to BW due to inflammatory hepatomegaly, characteristic of acute liver injury (FIG. 21, B). In contrast, all mice treated with the cocultured cells survived and showed a remarkable recovery pattern: the BW decreased for 1 or 2 days, followed by stability or an increase in BW to baseline. The lost BW had been regained by all treated mice by day 5 after $CCl_4$ injection (or day 4 after treatment with the cocultured cells). An increase in serum alanine transaminase (ALT) levels of all mice to greater than 350 times normal at 1 day after $CCl_4$ administration was observed (FIG. 21, C), indicating severe liver cell damage. On the day of sacrifice (day 7), the aspartate transaminase (AST) level, ratio of AST/ALT, and urea level were significantly higher in the control mice compared with treated mice (FIGS. 21, D and E). Analysis of the regional necrosis demonstrated a significant difference in the treated mice based on the necrotic cell count between the treated and control mouse livers (p<0.001; FIG. 21, F).

Consistently, histological analysis showed centrilobular necrosis characteristic of $CCl_4$ hepatic toxicity in the control mouse livers. Hepatocytes in the centrilobular region demonstrated vacuolar, hydropic, and fatty degeneration accompanied by pyknosis, karyorrhexis, and karyolysis in the control mouse livers on day 7 compared with normal livers. In contrast, the mice treated with the cocultured cells demonstrated complete regeneration with nearly normal structure in the central vein area. These results suggested that treatment using the cocultured cells markedly attenuates $CCl_4$ damage and greatly promotes liver regeneration. The inflammatory cells did not infiltrate the regenerated liver area and surrounding tissues after the treatment using the cocultured cells, suggesting little rejection or immune response occurs.

Fluorescent microscopy demonstrated considerable numbers of GFP+ cells in the central vein region, which is the target of $CCl_4$ injury. Transplanted GFP+ cells expressed albumin and the proliferation marker Ki-67. These results suggested that the transplanted cocultured cells are accepted by the host liver and are not transient, but actively proliferate and repopulate the damaged region both structurally and functionally. PCR analysis of the liver tissue showed the long-term presence of the GFP gene in the transplanted liver for at least 3 months. No gross or histologic evidence of hepatic tumor formation was found in the treated livers at all time points.

Example 8

Expression of Proliferation Markers, Growth Factors, and Cytokines

The following method was used to assess the expression levels of proliferation markers, growth factors, and cytokines in the activated stem cells. RT-PCR was performed to detect the expression levels of Cyclin D-1 (a proliferation marker), insulin-like growth factor 1 (IGF-1, a hormone that mediates the effects of growth hormone), insulin-like growth factor 1 receptor (IGF-1R, receptor of IGF-1), and growth factors and cytokines such as transforming growth factor alpha (TGF-α), vascular endothelial growth factor (VEGF), and Notch-1. The 18S rRNA was used as an internal control. The levels of growth factors and cytokines were also evaluated by IF and other methods.

Figure 22:
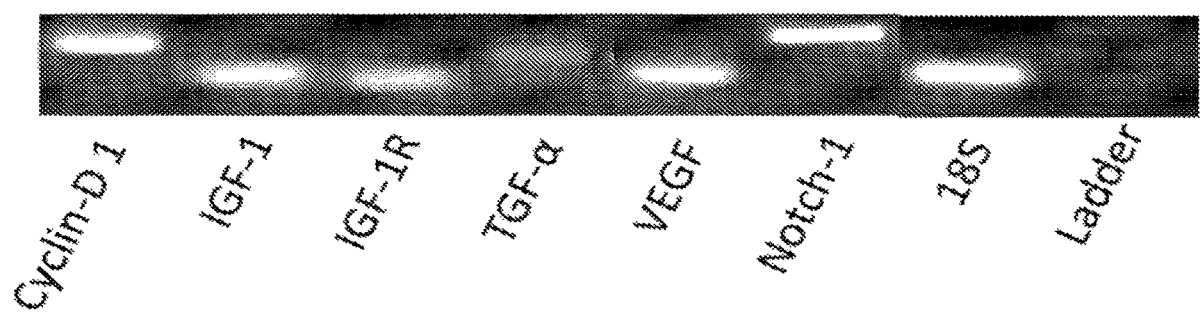
FIG. 22 is an illustration showing expression of proliferation markers, growth factors, and cytokines of the activated stem cells.

The results were demonstrated in FIG. 22. High expression level of cyclin D-1 was shown, indicating that the activated stem cells are rapidly proliferating. The expression of both IGF-1 and its receptor IGF-1R indicated that the proliferation of the activated stem cells may be regulated by autocrine mechanism. The activated stem cells were also shown to express TGF-α, VEGF, and Notch-1. IF results also showed expression of hepatocyte growth factor (HGF) and fibroblast growth factor 9 (FGF9) in the activated stem cells.

Example 9

Tumorigenicity Test

The following method was used to assess the tumorigenicity of the activated stem cells. Five nude mice, 10-week-old, were injected subcutaneously with 1 million activated stem cells. Renal capsule injection with 1 million activated stem cells was performed to five nude mice, 10-week-old. On day 1 (D1) after injection, luciferase assay was performed to track the activated stem cells in situ. Continuous observation was performed for 3 months after injection. At the end of three months, the nude mice were sacrificed to evaluate tumorigenesis effects and to locate the injected activated stem cells in situ. The tissues and organs of the whole body of the nude mice were examined using pathological method. The results demonstrated that the activated stem cells is non-tumorigenic in the whole body.

What is claimed is:

1. A method for preparing a plurality of cells, comprising:
isolating, from a blood sample, a plurality of CD45+ cells, wherein each of the cells of the plurality of CD45+ cells has a diameter of less than 5 μm, and each of the cells of the plurality of CD45+ cells is further characterized as ABCG2− and CD34+; and
activating the plurality of CD45+ cells, by culturing the plurality of CD45+ cells in
a medium that
(a) comprises primary hepatocytes or cells of a hepatocyte cell line, or
(b) has been conditioned with primary hepatocytes or cells of a hepatocyte cell line, for at least 4 hours, to become CD45-cells that are further characterized as ABCG2+.

2. The method of claim 1, wherein each of the cells of the plurality of CD45+ cells has a diameter of less than 3 μm.

3. The method of claim 1, wherein each of the cells of the plurality of CD45+ cells comprises small RNA and ribosomal RNA at a ratio of at least 20:1.

4. The method of claim 1, wherein each of the cells of the plurality of CD45+ cells has a nucleus to cytoplasm ratio (v/v) that is at least 9:1.

5. The method of claim 1, wherein the hepatocyte cell line comprises AML 12, HepaRG, or the combination thereof.

6. The method of claim 1, wherein the CD45⁻ cells are capable of developing into a colony during culturing in vitro.

* * * * *

UNITED STATES PATENT AND TRADEMARK OFFICE
CERTIFICATE OF CORRECTION

| | | |
|---|---|---|
| PATENT NO. | : 12,203,096 B2 | Page 1 of 1 |
| APPLICATION NO. | : 17/953216 | |
| DATED | : January 21, 2025 | |
| INVENTOR(S) | : Shaowei Li et al. | |

It is certified that error appears in the above-identified patent and that said Letters Patent is hereby corrected as shown below:

In the Specification

In Column 1, below the section CROSS REFERENCE TO RELATED APPLICATIONS, Line 15, please insert the text:
-- STATEMENT REGARDING FEDERALLY SPONSORED RESEARCH OR DEVELOPMENT
This invention was made with Government support under contract GM087609 awarded by the National Institutes of Health. The Government has certain rights in the invention. --.

Signed and Sealed this
Eleventh Day of November, 2025

John A. Squires
*Director of the United States Patent and Trademark Office*